(12) United States Patent
Modi et al.

(10) Patent No.: US 11,424,039 B1
(45) Date of Patent: Aug. 23, 2022

(54) GENERATING EASY-TO-UNDERSTAND GRAPHS OF LARGE DATA SETS

(71) Applicant: CAPITOL AI, INC., San Mateo, CA (US)

(72) Inventors: Shaun Modi, Washington, DC (US); Thomas Hallaran, Madison, WI (US); Tong Lee, Gardiner, NY (US); Lipsa Panda, New York, NY (US); Varun Gupta, Brooklyn, NY (US)

(73) Assignee: Capitol AI, Inc., San Mateo, CA (US)

( * ) Notice: Subject to any disclaimer, the term of this patent is extended or adjusted under 35 U.S.C. 154(b) by 0 days.

(21) Appl. No.: 17/575,130

(22) Filed: Jan. 13, 2022

(51) Int. Cl.
*G16H 50/70* (2018.01)
*G06T 11/20* (2006.01)
*G16H 50/30* (2018.01)

(52) U.S. Cl.
CPC .......... *G16H 50/70* (2018.01); *G06T 11/206* (2013.01); *G16H 50/30* (2018.01)

(58) Field of Classification Search
CPC ....... G16H 50/70; G16H 50/30; G06T 11/206
USPC ...................................................... 705/2–3
See application file for complete search history.

(56) References Cited

U.S. PATENT DOCUMENTS

| | | | |
|---|---|---|---|
| 9,418,457 B1 | 8/2016 | Glover | |
| 10,042,959 B2 | 8/2018 | Sexton | |
| 10,706,061 B2 | 7/2020 | Sherman | |
| 10,895,972 B1 * | 1/2021 | Apostolatos | .......... G06T 11/206 |
| 2011/0288877 A1 * | 11/2011 | Ofek | ...................... G16H 50/20 |
| | | | 707/661 |
| 2015/0278214 A1 | 10/2015 | Anand | |
| 2015/0310643 A1 | 10/2015 | Rzeszotarski | |
| 2019/0220524 A1 * | 7/2019 | Costabello | ............. G06N 5/045 |
| 2020/0126282 A1 | 4/2020 | Moroze | |
| 2021/0049797 A1 * | 2/2021 | Cervelli | ................ G06F 16/904 |
| 2021/0117051 A1 * | 4/2021 | McRaven | ............ G06T 11/206 |
| 2021/0233295 A1 | 7/2021 | Indurkhya | |
| 2022/0067273 A1 | 3/2022 | Shin | |

* cited by examiner

*Primary Examiner* — Michael Tomaszewski
(74) *Attorney, Agent, or Firm* — Perkins Coie LLP

(57) ABSTRACT

Disclosed is a system to obtain the data set including multiple variables. The system extracts the multiple variables from the data set. Based on the data set, the system creates an ontology indicating multiple relationships between two or more variables among the multiple variables, where a relationship among multiple relationships indicates a correlation between the two or more variables. The system obtains an intent associated with the user, and a visualization standard, where the visualization standard indicates an attribute associated with the visualization. The system generates a sequence of multiple visualizations to present to the user by ranking the multiple visualizations based on the correlation between the two or more variables, the visualization standard and the intent associated with the user. The system presents the sequence of multiple visualizations based on the ranking.

26 Claims, 22 Drawing Sheets

GENERATING EASY-TO-UNDERSTAND GRAPHS OF LARGE DATA SETS

BACKGROUND

Today's technology enables users to gather and store vast amounts of data. However, to draw value from the data, the data needs to be analyzed and presented in a format understandable by people, such as healthcare workers, who may not necessarily be versed in mathematics and statistical analysis.

BRIEF DESCRIPTION OF THE DRAWINGS

Detailed descriptions of implementations of the present invention will be described and explained through the use of the accompanying drawings.

Figure 1:
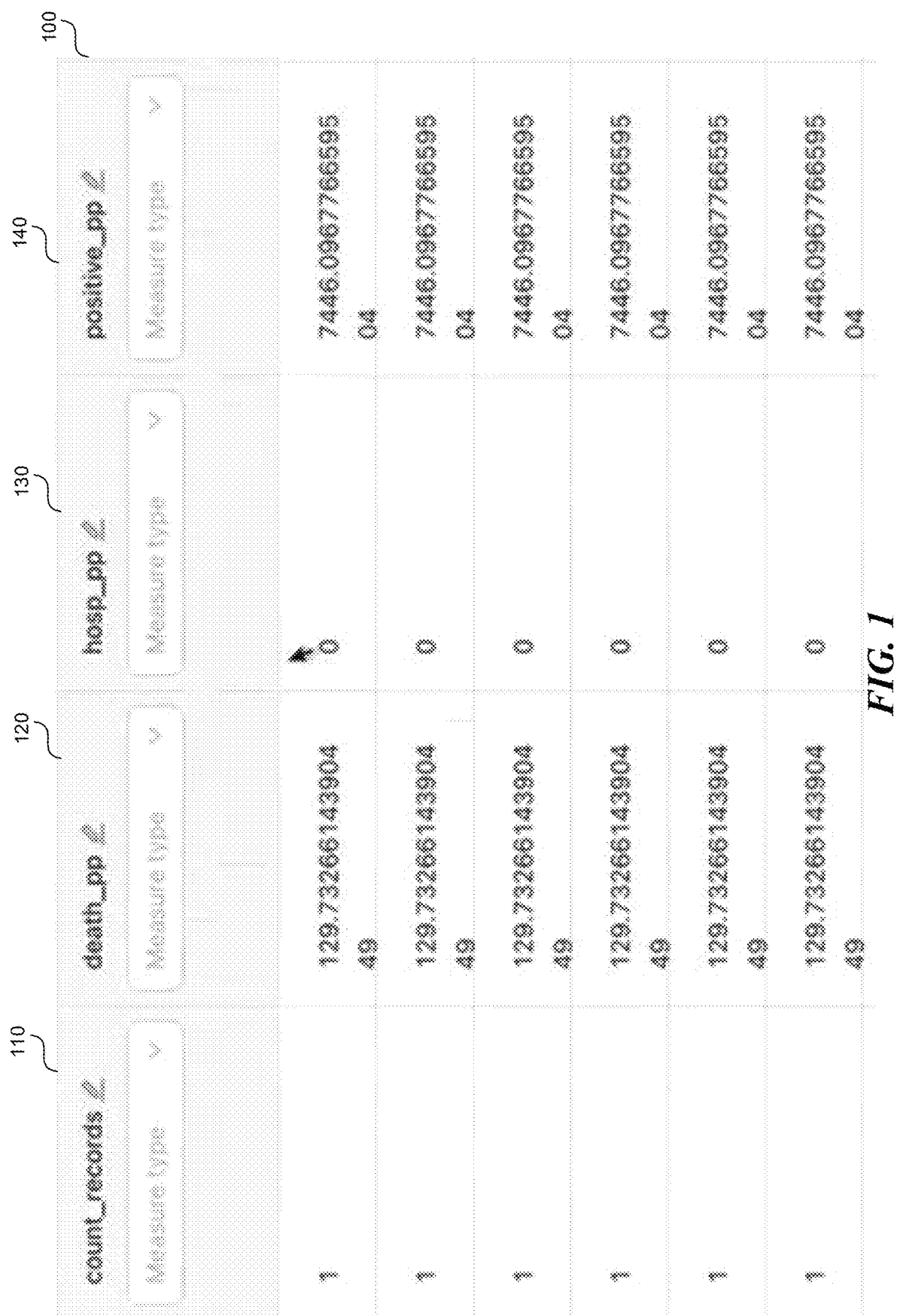
FIG. 1 shows an imported data set.

The technologies described herein will become more apparent to those skilled in the art from studying the Detailed Description in conjunction with the drawings. Embodiments or implementations describing aspects of the invention are illustrated by way of example, and the same references can indicate similar elements. While the drawings depict various implementations for the purpose of illustration, those skilled in the art will recognize that alternative implementations can be employed without departing from the principles of the present technologies. Accordingly, while specific implementations are shown in the drawings, the technology is amenable to various modifications.

DETAILED DESCRIPTION

Disclosed here is a system and method to generate a visualization of at least a portion of a data set, such as a healthcare, marketing, product or other data set. The system can obtain the data set including multiple variables, such healthcare data for the number of COVID-19 deaths per county in the United States. The system extracts the multiple variables from the data set. Based on the data set, the system can create an ontology indicating multiple relationships between two or more variables among the multiple variables. The relationship in the ontology can indicate a correlation between the two or more variables, whether the correlation is positive or negative. The system can obtain an intent associated with the user, where the intent indicates visualizations frequently viewed by the user. The system can highly prioritize visualizations similar to the visualizations frequently viewed by the user.

The system can obtain a visualization standard, where the visualization standard indicates representing categorical variables using a bar graph, and representing numerical variables using a scatterplot. Based on the ontology, the intent, and the visualization standard, the system can generate an ordered sequence of multiple visualizations to present to the user. To generate the ordered sequence of multiple visualizations, the system can determine the multiple visualizations to present to the user by determining multiple permutations of the two or more variables. A permutation of the two or more variables corresponds to a visualization among the multiple visualizations. Each permutation assigns a variable to either the X- or the Y-axis. The system can rank the multiple visualizations based on the correlation between the two or more variables, the visualization standard, and the intent associated with the user. The system can present the sequence of multiple visualizations based on the ranking, where the higher ranked visualizations are presented first.

The description and associated drawings are illustrative examples and are not to be construed as limiting. This disclosure provides certain details for a thorough understanding and enabling description of these examples. One skilled in the relevant technology will understand, however, that the invention can be practiced without many of these details. Likewise, one skilled in the relevant technology will understand that the invention can include well-known structures or features that are not shown or described in detail, to avoid unnecessarily obscuring the descriptions of examples.

FIG. 1 shows an imported data set. The imported data set 100 can be represented by various formats such as a comma separated value (CSV), excel or semi structured format. The imported data set 100 can contain multiple variables 110, 120, 130, 140, etc. (only four shown for brevity) that can be represented by columns or rows in the imported data set 100. The imported data set 100 can contain data from various industry sectors such as healthcare, telecommunications, policing, marketing, etc. The imported data sets 100 can contain gigabytes or terabytes of data, which is impossible for a person to absorb, analyze, and understand. The disclosed system and method aid in analyzing the data, identifying important relationships, creating the easy-to-understand visualizations of the important relationships in the data, and creating stories based on the visualizations.

Figure 2A:
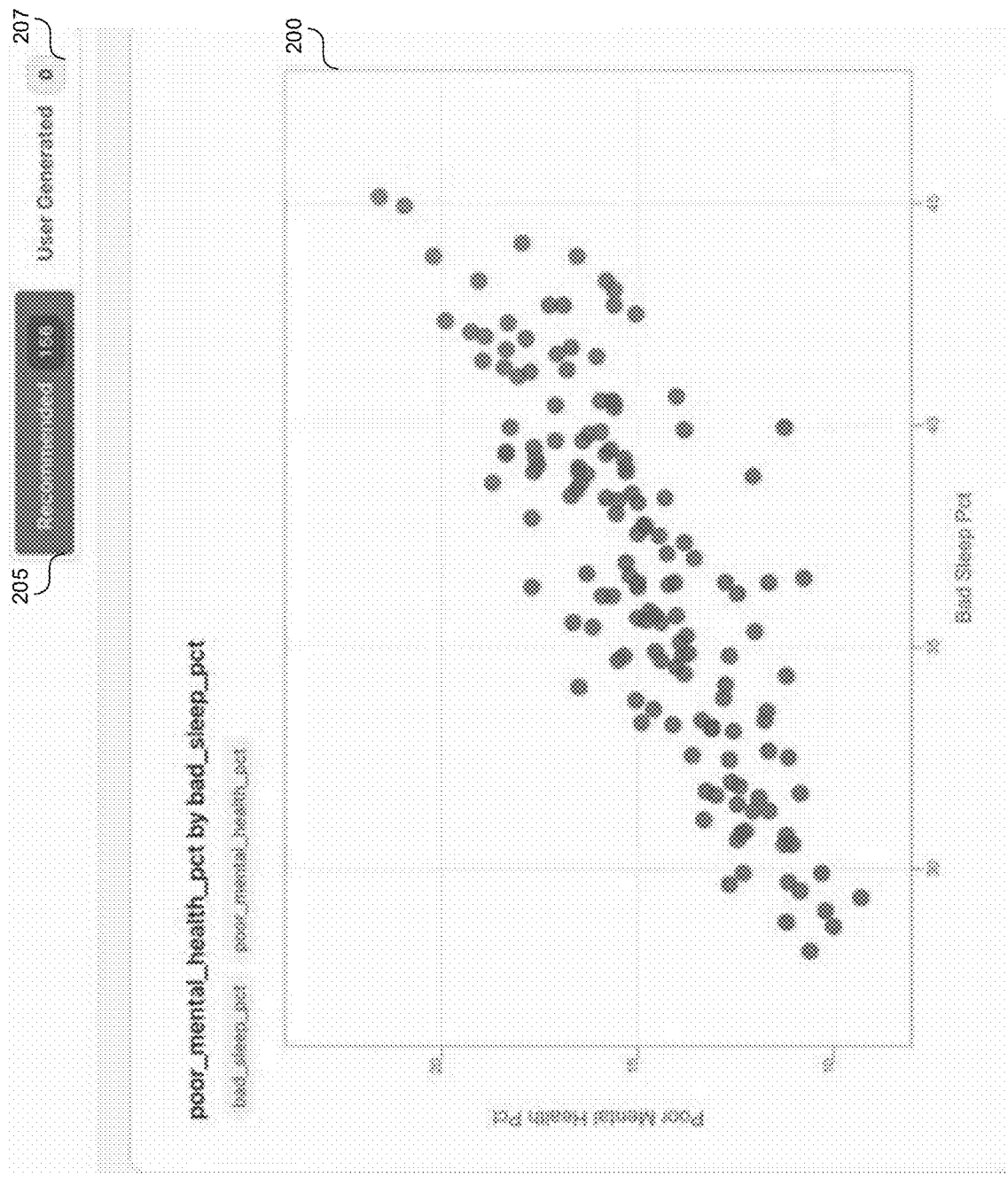
FIGS. 2A-2C show visualizations produced by the system.
Figure 2B:
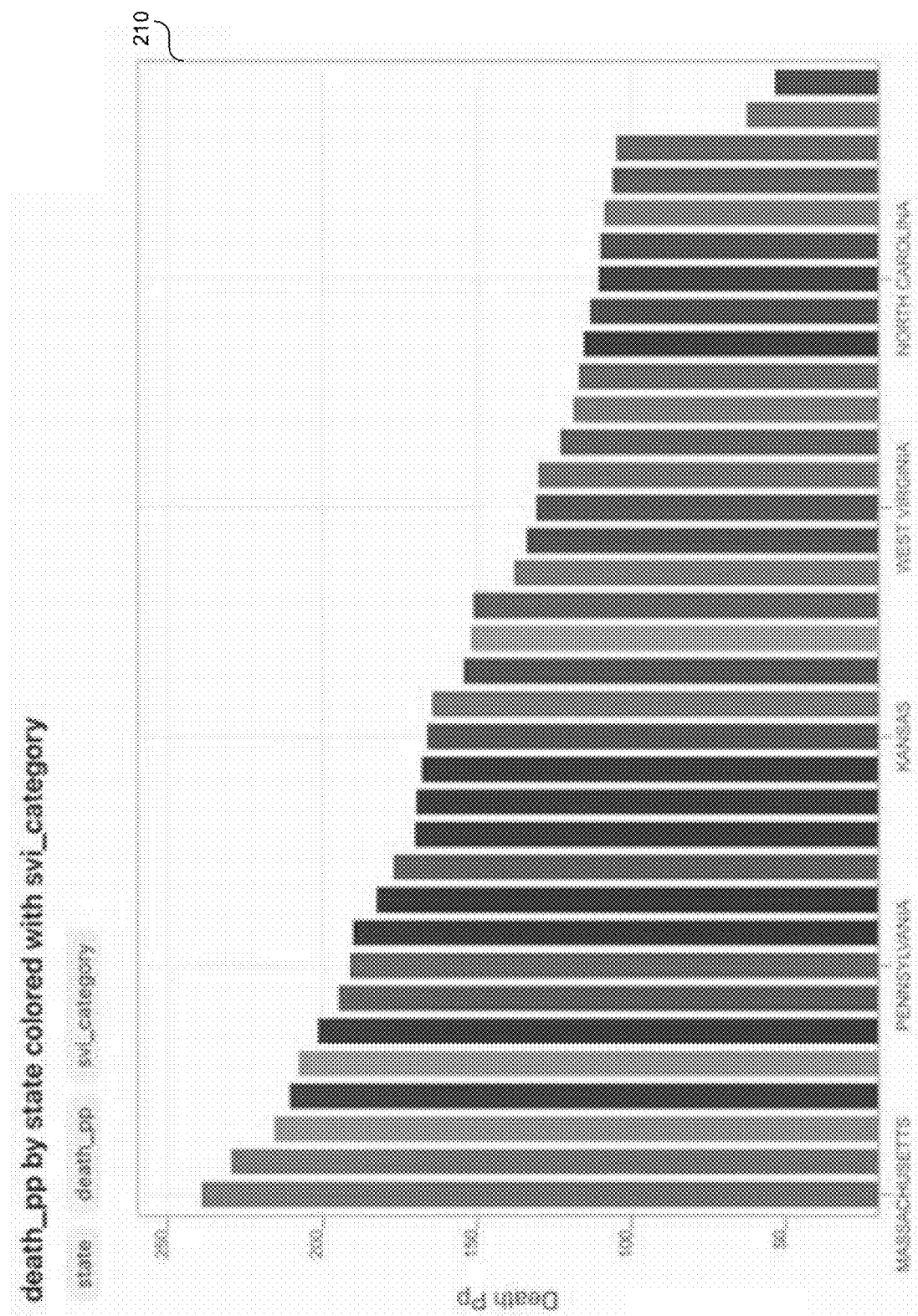
Figure 2C:
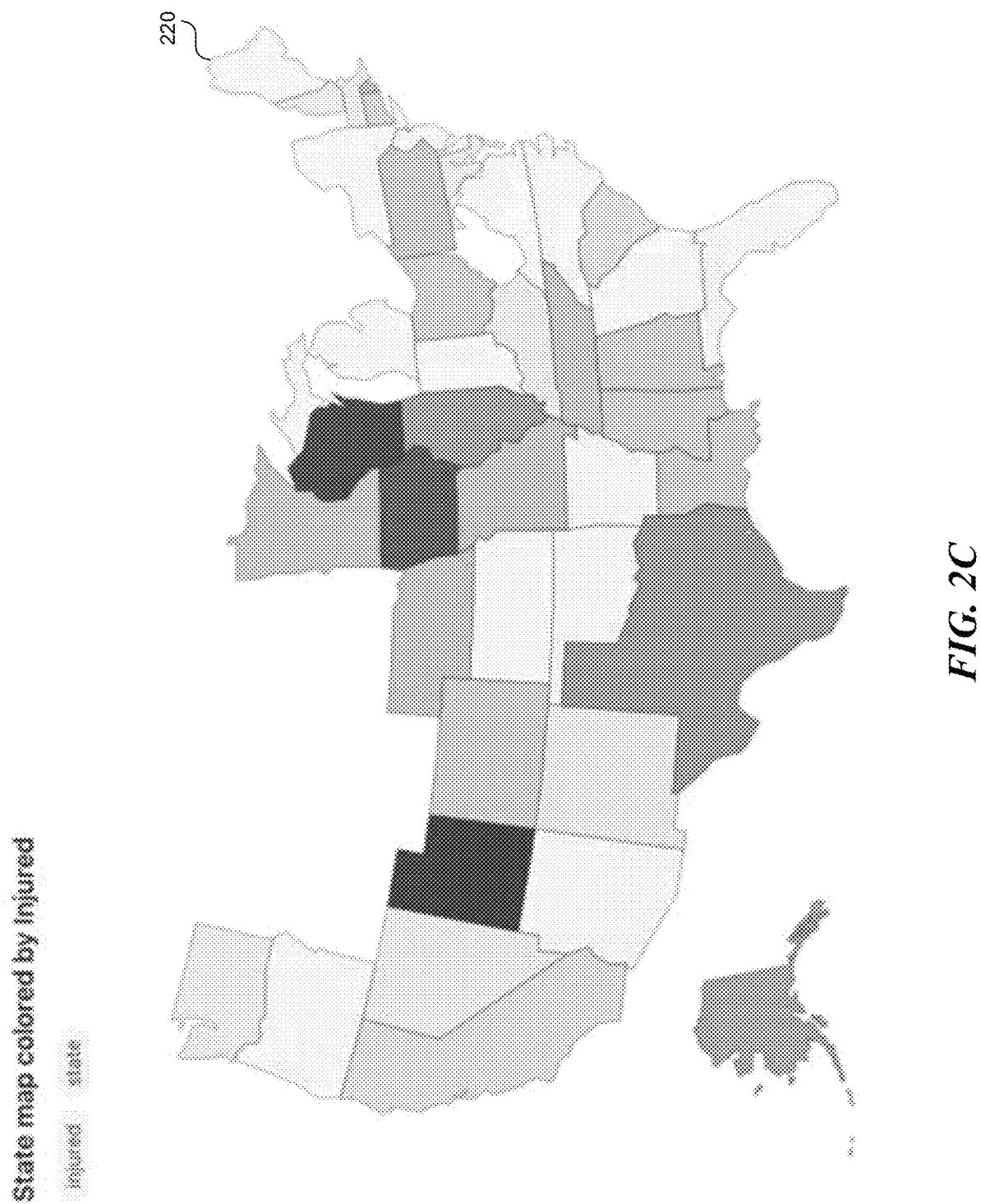

FIGS. 2A-2C show visualizations produced by the system. The data set shown in the visualizations 200, 210, 220 contains 23 variables. This is a relatively small table, but the visualization space that can be generated from those 23 variables is greater than 4.1515867E+12. This is a very large number that would make exploring the visualization space extremely cumbersome for the user. However, some visualizations are more informative than others. The system disclosed here filters out the visualizations that are not useful and generates only the most informative visualizations, ranks them, and displays them in order. For example, in the above set containing 23 variables, the system narrows down the important visualizations to 156, as shown in element 205. The visualizations can be a line graph, donut chart, scatterplot 200, a bar graph 210, or a chloropleth map 220.

In addition to the generated visualizations, as shown in FIG. 2A, the user interface element 207 enables the user to generate a visualization that has not been provided by the system. The user can specify the variables and the type of visualization to generate, and the system can generate the user-specified visualization.

A choropleth map is a type of thematic map in which a set of pre-defined areas is colored or patterned in proportion to a statistical variable that represents an aggregate summary of a characteristic within each area, such as population density or per-capita income visualized in relation to geography. In choropleth 220, the geographic area is a state. However, other geographic areas can be represented, such as counties, zip codes, cities, countries, continents, etc. The system can automatically determine the geographical area via type inference and fuzzy matching. For example, the system can determine whether the geographical area includes county, city, state, country, or continent. The system uses string comparison algorithms such as the Levenshtein algorithm to produce matching inferences.

Figure 3:
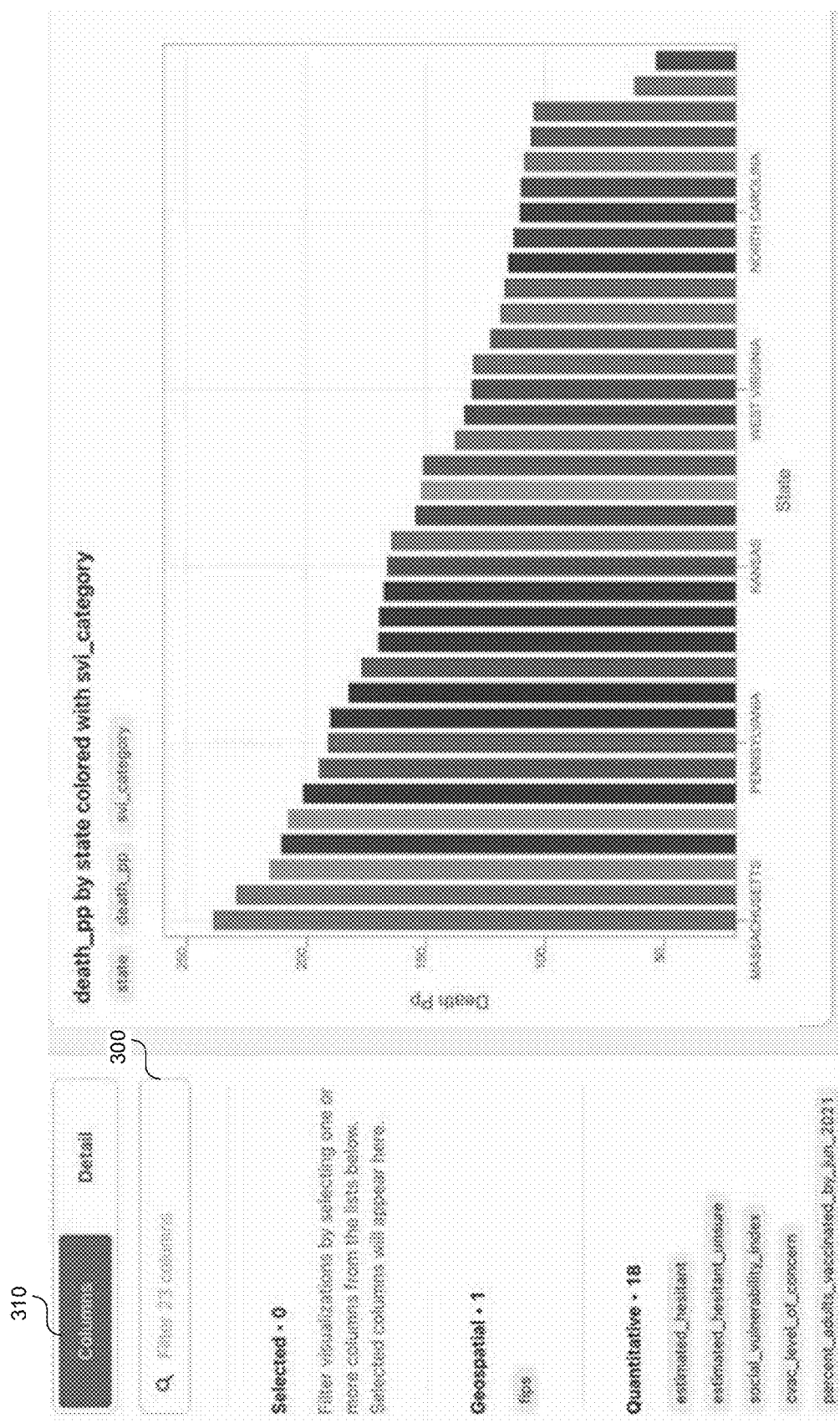
FIG. 3 shows a user interface to navigate the visualizations.

FIG. 3 shows the user interface to navigate the visualizations. The user interface element 300 enables the user to search the visualizations. The user interface element 310 enables a user to indicate an aspect of the visualization that the user is interested in, such as the name of the variable. The name of the variable can correspond to the name of the column in the imported data set 100 in FIG. 1. Once the user specifies the name of the variable, the system can provide the visualizations including the named variable. Alternatively, the user can specify the type of a visualization such as a scatterplot, a bar graph, or a choropleth. In addition, the system can lay out the visualizations for user viewing such that the user does not have to horizontally scroll to view the visualizations.

The system can enable the user to combine two or more data sets. The system can generate visualizations, as described in this application, for the two or more data sets and can allow the user to drag and drop visualizations from the first data set into the second data set, thereby introducing the variables presented in the dragged-and-dropped visualizations into the second data set.

Figure 4A:
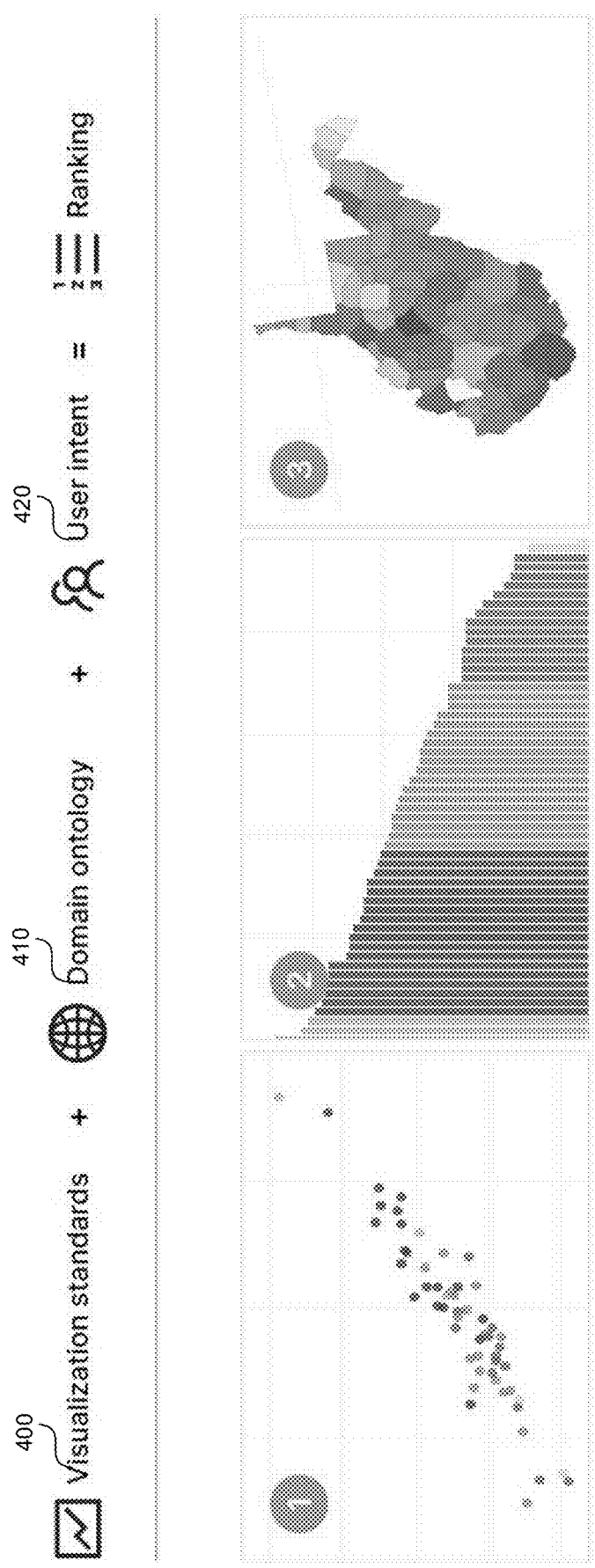
FIG. 4A indicates a method to rank the visualizations.

FIG. 4A indicates a method to rank the visualizations. The visualizations that are generated by the system, as described in this application, are ranked according to relevance to the user and presented to the user in a ranked order. To rank the visualizations, the system considers visualization standards 400, ontology 410, and user intent 420.

The visualization standards 400 indicate preferences such as displaying a time variable on the X-axis as opposed Y-axis, or limiting the number of colors presented in a visualization to a predetermined number, such as 20. The visualization standard 400 can also indicate that geospatial data is visualized using a choropleth, categorical variables are visualized using a bar graph, and numeric variables are visualized using a scatterplot. A categorical variable has values that can be put into a countable number of distinct groups based on a characteristic. For a categorical variable, the categories have no natural order. Numeric variables have values that describe a measurable quantity as a number, like "how many" or "how much".

The system can determine the user intent 420 based on the user's proficiency with viewing visualizations, based on the role the user has in the system (editor, analyst, business stakeholder, viewer, collaborator), based on the task the user is performing, and/or based on previously viewed charts, and based on the collected data on the historical use of the system, etc. For example, the system can store a profile indicating all users' and the specific user's proficiency and frequently viewed charts. From this collected data, the system generates a user intent model.

Based on use the user intel model, the system can generate 2D, 3D, 4D, 5D, etc., visualizations indicating relationships between 2, 3, 4, 5, etc., variables, respectively. If the user is highly proficient, such as the user is a frequent user of the system, the system can generate appropriate visualizations indicating relationships between multiple variables.

If the user frequently views choropleths, the system can rank choropleth charts higher. If the user frequently views highly coherent data, the system can rank visualizations containing highly coherent variables higher, etc.

Figure 4B:
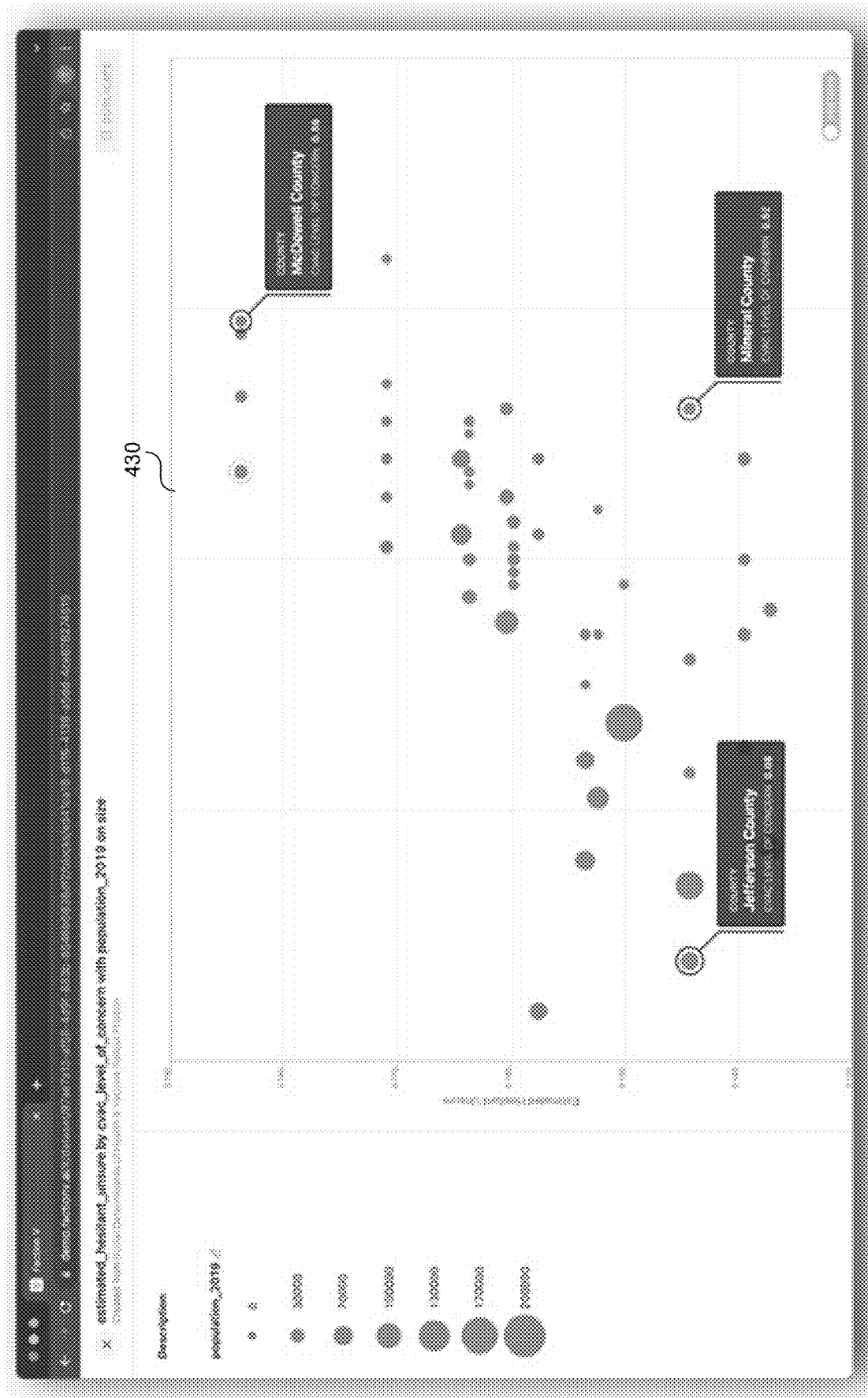
FIG. 4B shows a visualization of high variability data.

FIG. 4B shows a visualization of high variability data. The task the user is performing can be opportunity analysis. Opportunity analysis refers to establishing demand and competitive analysis, and studying market conditions to be able to have a clear vision and plan strategies accordingly. Opportunity analysis is a vital process for the growth of an organization and needs to be performed frequently. For the users performing an opportunity analysis task, the system can identify visualizations that have a high amount of variation and/or dispersion, such as visualization 430. The system can highly rank visualizations showing a high amount of variation and/or dispersion.

Another example of a task performed by the user can be analyzing Medicaid data for a particular state. The system can automatically highly rank the visualizations showing data for the particular state.

To determine the user's intent, the system can use artificial intelligence/machine learning (AI/ML) to automatically determine the types of visualizations relevant to the user by analyzing the types of visualizations saved and shared by users. The system can gather logs of data based on user interaction with the system, which can be fed into an AI/ML system.

Figure 5:
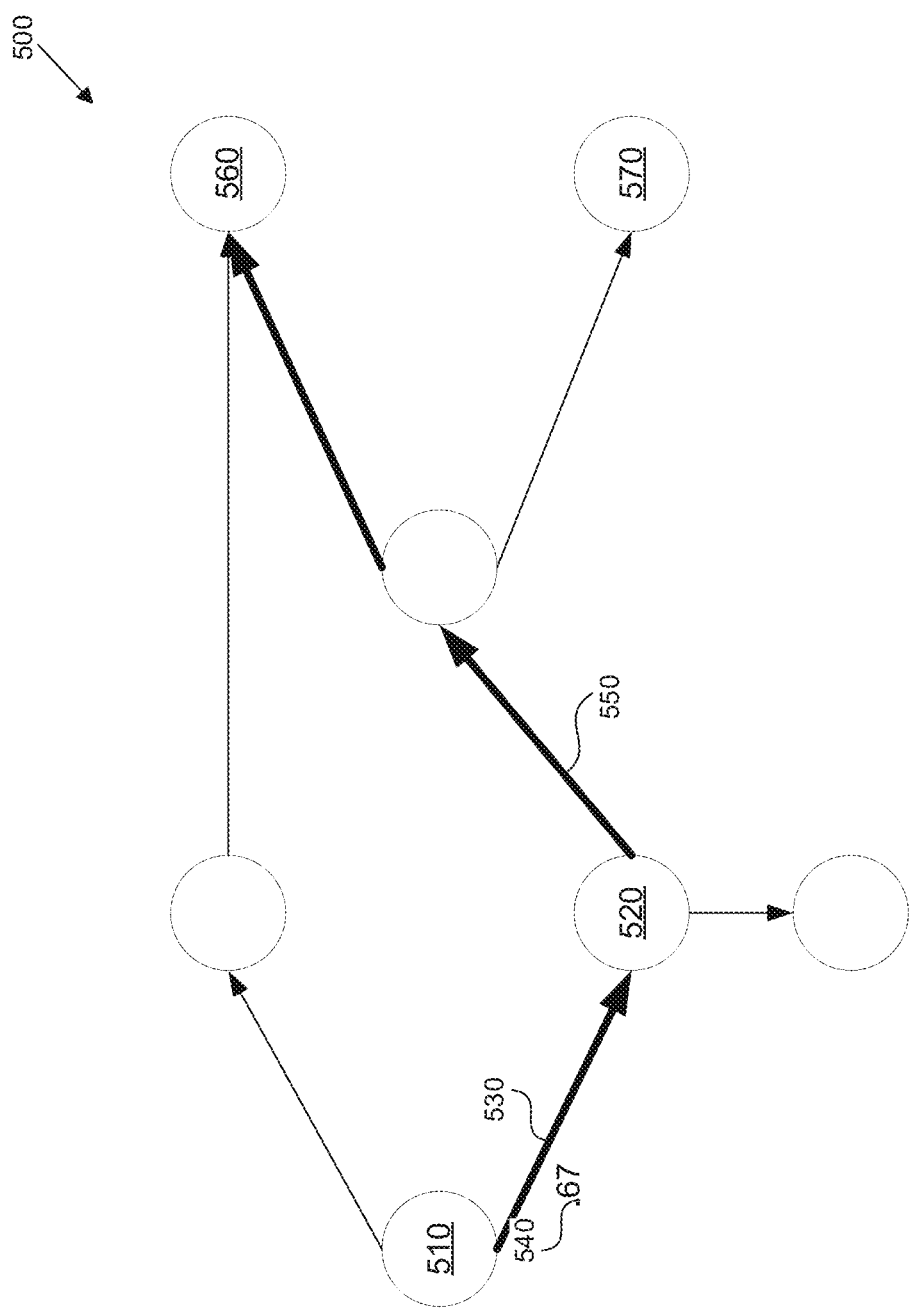
FIG. 5 shows an ontology that can be used in ranking the visualizations.

FIG. 5 shows an ontology that can be used in filtering the total visualization space as well as ranking visualizations. The ontology can be represented as a directed acyclic visualization (DAG) 500. Each node 510, 520, 560, 570 (only four labeled for brevity) in the DAG can correspond to a variable 110, 120, 130, 140 in FIG. 1. Each edge 530 (only one labeled for brevity) can represent a correlation between two nodes 510, 520. Nodes that have zero correlation between each other do not have an edge connecting them, such as nodes 560, 570. Nodes that are connected by an edge path 550 in the DAG 500 can be represented in a visualization. The edge 530 can have a weight 540 which can indicate the strength of the correlation between two nodes 510, 520. The system includes an algorithm for creating ontologies that leverages meta data from data catalog repositories that exist in the public domain and in many organizations. The system can ingest this meta data or a subset of this meta data to create a DAG that is specific to a given domain of knowledge.

The system can automatically create the DAG 500 by measuring correlation between variables in the imported data set 100 in FIG. 1. Alternatively, the system can look at the metadata associated with the imported data set 100 to generate the DAG 500. For example, the metadata can indicate a relationship between variables, which the system can translate into edges in the DAG 500. Subsequently, the system can present the automatically generated DAG 500 to a user, and the user can then modify the DAG. The system can, also, employ an AI/ML to generate the DAG 500.

The system can automatically identify independent versus dependent variables. For example, a person data set is independent of a COVID vaccination data set, which is dependent on the person. Once identified, the visualizations can contain the independent variable on the X-axis and the dependent variable on the Y-axis. The system can also use metadata to identify independent and dependent variables. To the dependency between the variables can be represented by using the direction of the edge 530, where the independent variable is the source and the dependent variable is the sink associated with the edge. The system tests sets of variables that are dependent and independent for correlation. Correlation is used as an input to the ranking algorithm.

The DAG 500 can also indicate which variables can be aggregated. For example, the DAG 500 can indicate that variables that are connected by a path 550 can be aggregated with functions such as group by, average, sum and count and shown as a single variable in a visualization.

To rank the variables, as described in FIG. 4, the system can highly rank the variables with high correlation, whether positive or negative. In addition, the system can detect outliers in the data, and highly rank the visualizations containing outliers.

Figure 6A:
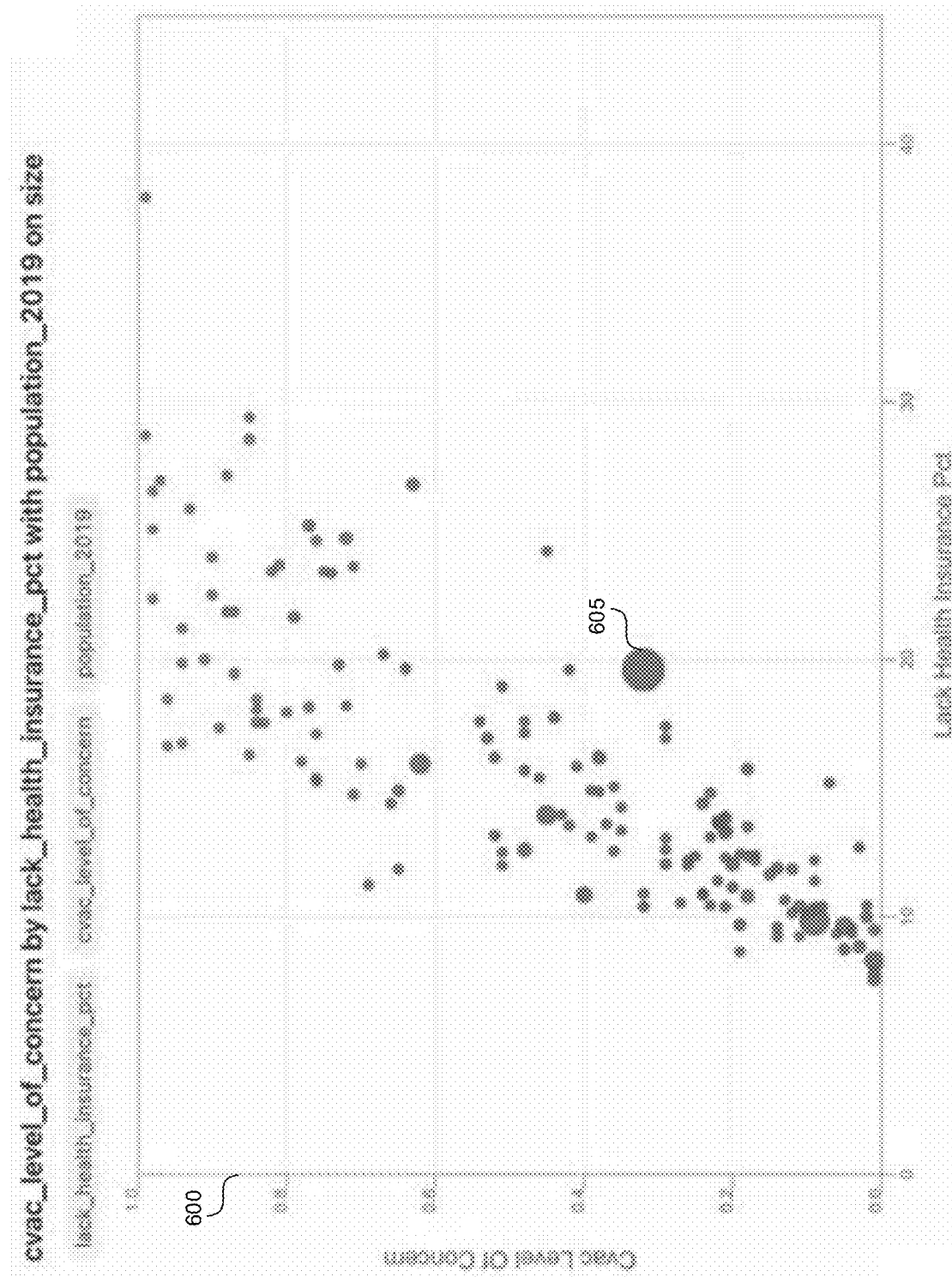
FIGS. 6A-6C show techniques to visualize three or more variables in a two-dimensional visualization.
Figure 6B:
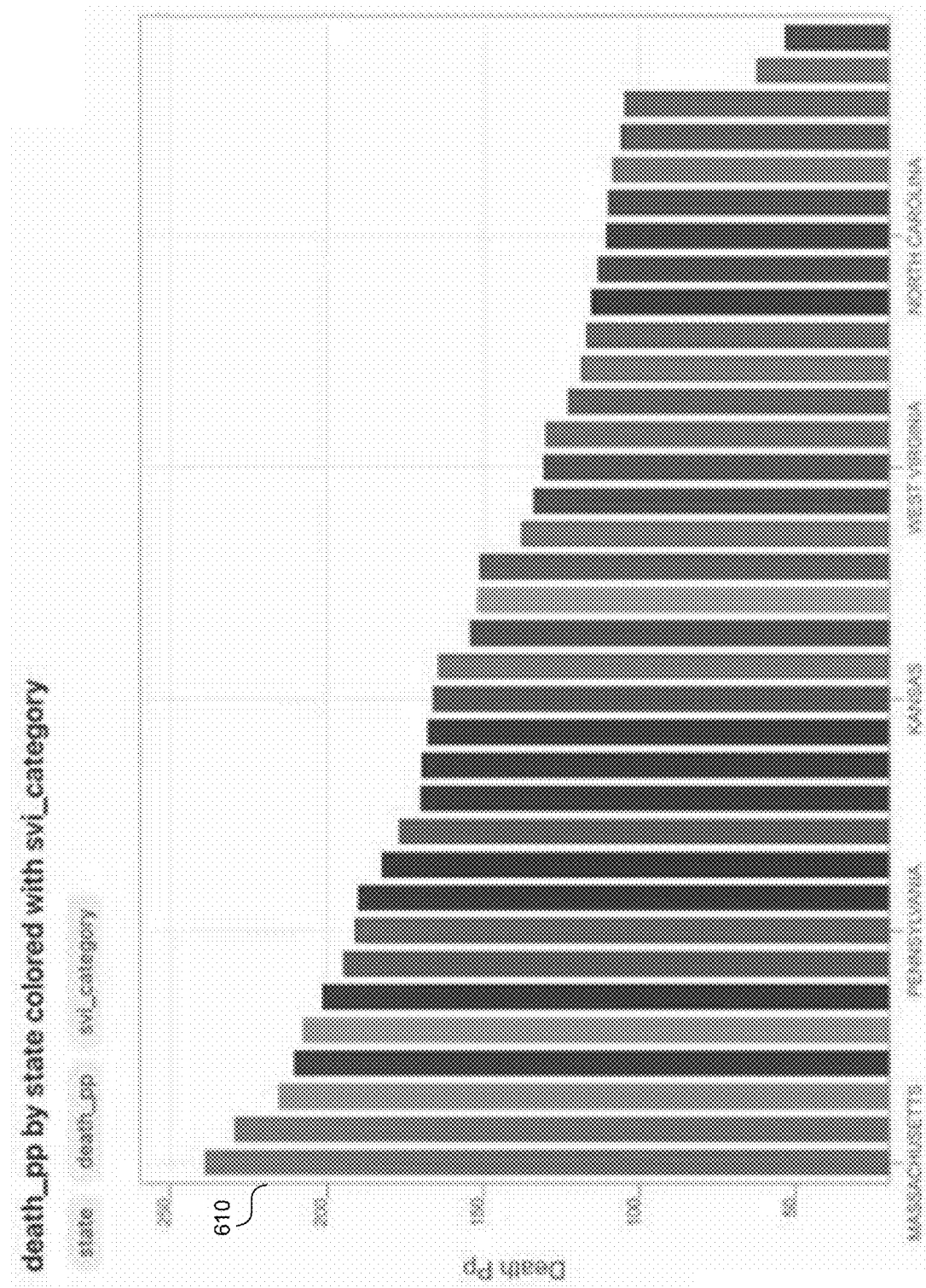
Figure 6C:
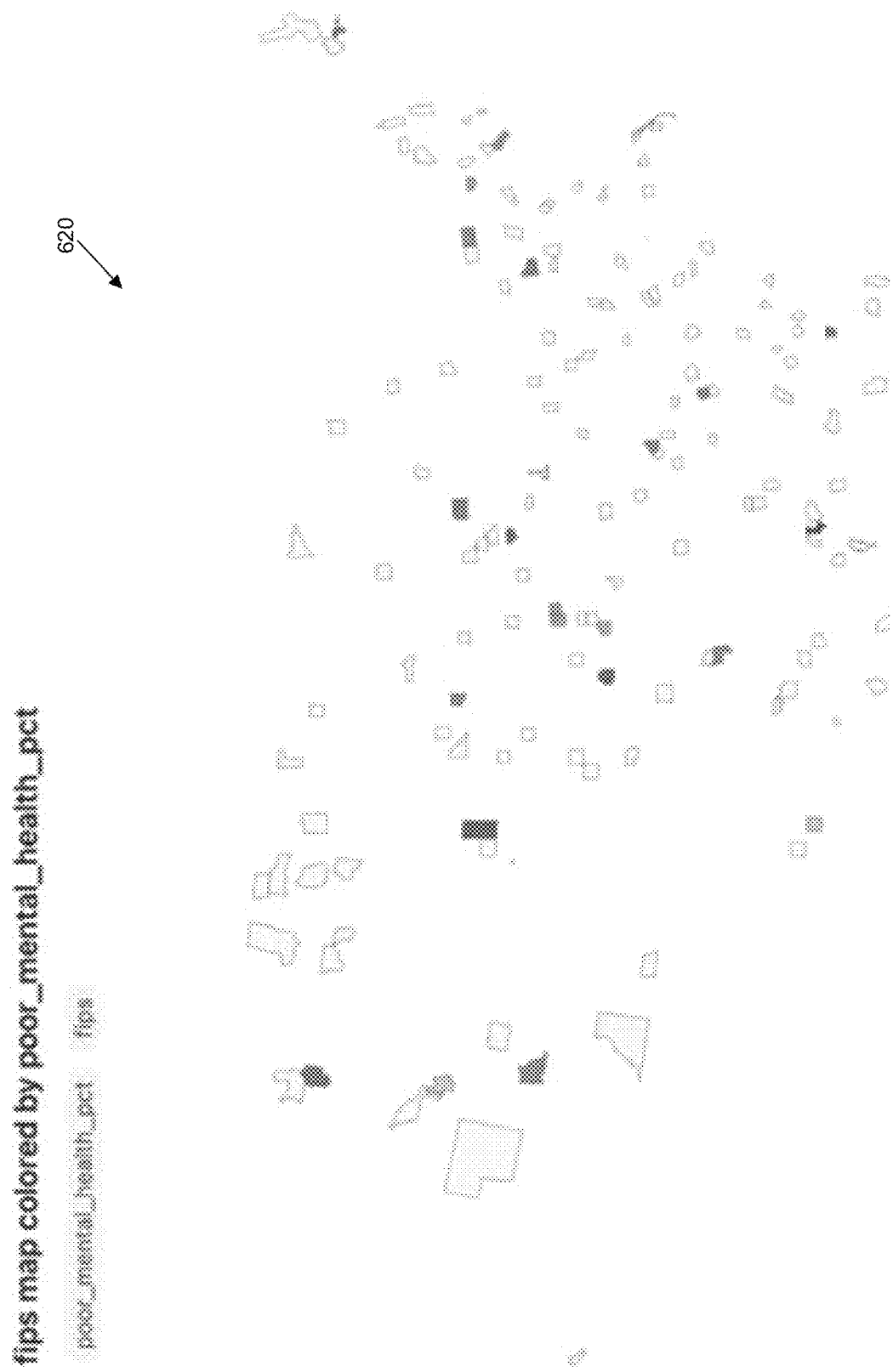

FIGS. 6A-6C show techniques to visualize three or more variables in a two-dimensional visualization. The visualizations 600, 610, 620 are all two-dimensional graphs. However, using other attributes of the visualizations such as size, color, and opacity, additional variables can be visualized in a two-dimensional graph.

For example, in FIG. 6A, visualization 600 shows three variables in a two-dimensional visualization, namely, lack of health insurance, vaccination level, and county population. The lack of health insurance is shown on the X-axis, vaccination level is shown in the Y-axis, while the county population is indicated by the size of the dot. For example, the county represented by point 605 has the highest population.

In FIG. 6B, visualization 610 shows three variables in a two-dimensional visualization, namely, states on the X-axis, death per population of the Y-axis, and social vulnerability index by color. In FIG. 6C, visualization 620 uses opacity to indicate mental health of population using a choropleth. Size, color, and opacity can be combined to show up to five variables in a single visualization.

The system can represent attributes, size, color, and opacity using a predetermined range for each attribute. The system can obtain the range for each variable to be represented by each attribute. The system can map the range of each attribute to the range of each variable to determine which color, opacity, and or size to use for which variable value.

When choosing whether to represent a third variable using color, opacity or size, the system can use a visualization standard 400 in FIG. 4. The visualization standard can indicate the preferred ranking of attributes, which can indicate that opacity is less preferred than color and size.

Figure 7A:
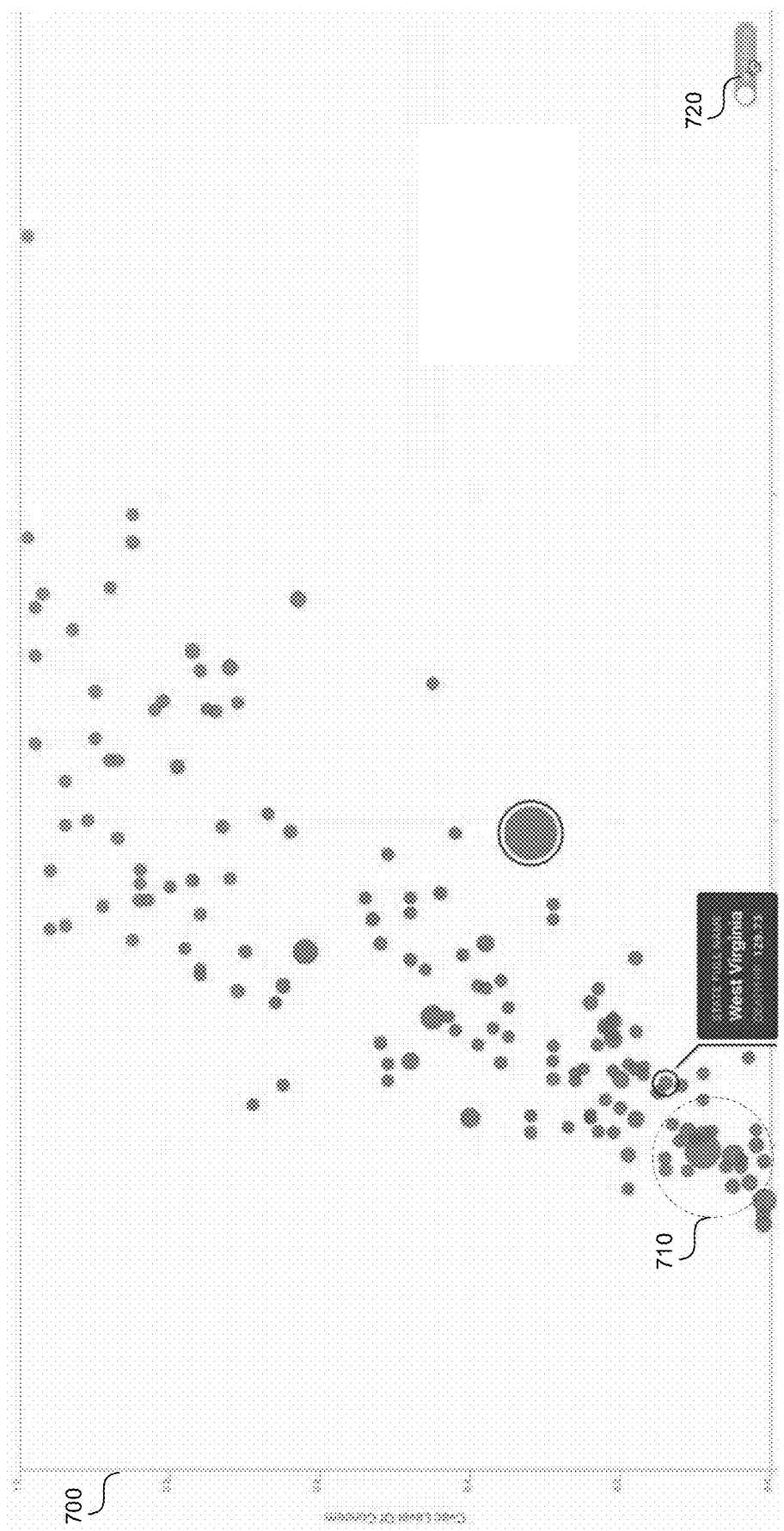
FIGS. 7A-7B show use of a force spread to generate a scatterplot.
Figure 7B:
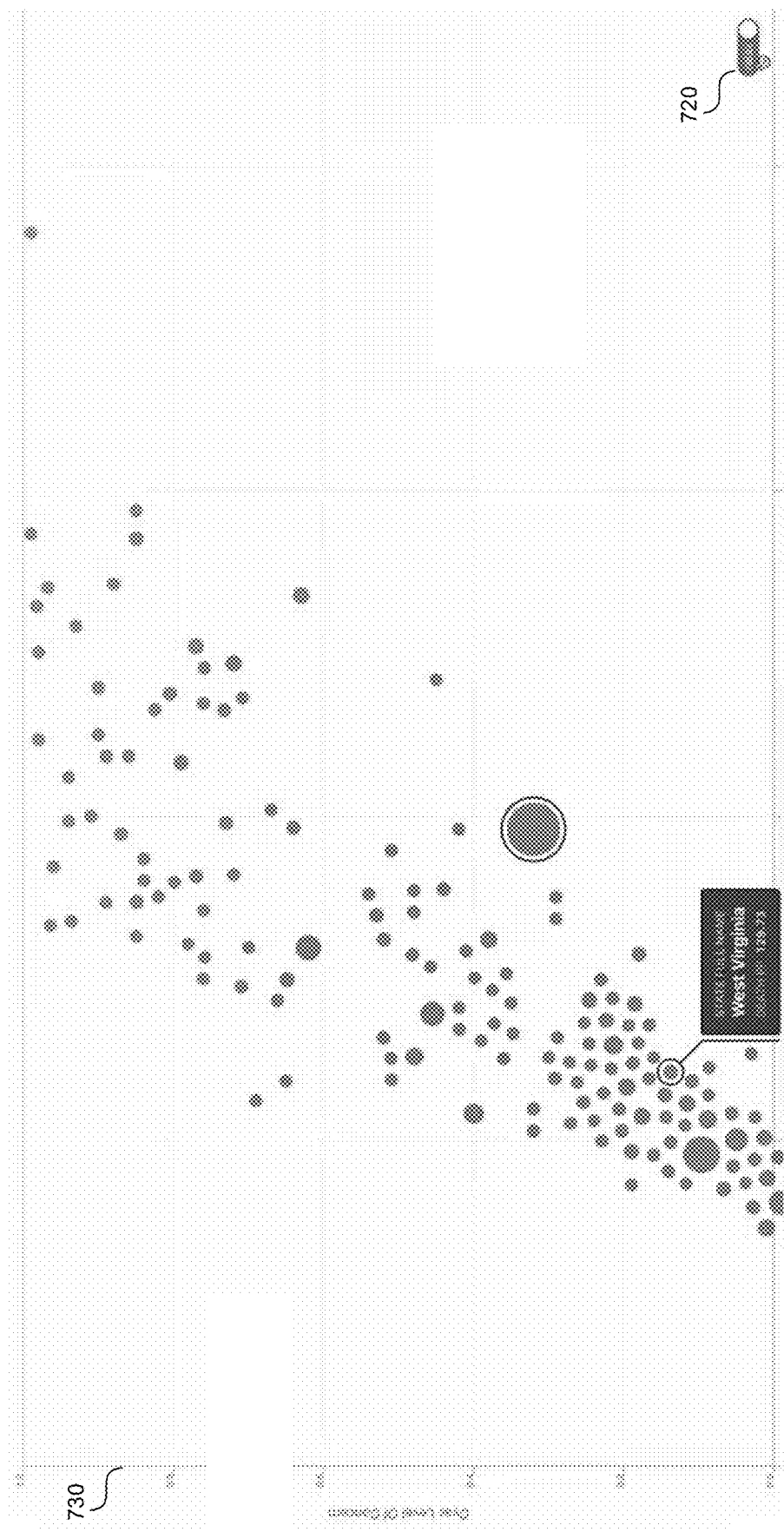

FIGS. 7A-7B show use of a force spread to generate a scatterplot. As can be seen in FIG. 7A, scatterplot 700 contains regions 710 (only one labeled for brevity) of overlap between data points. To remove the overlap, the user can select the user interface element 720, which can indicate to the system to resolve overlaps between data points. As can be seen in FIG. 7B, scatterplot 730 does not contain overlapping data points.

The system can use a particle simulation algorithm to perform the spreading whereby points are spread from one another based on their relative size. The system can use an animation algorithm to animate that spread. The system can use opposite algorithms to revert back to a relaxed display. Such an algorithm can help users see or appreciate congested or clustered data points where at least some displayed data points overlap other displayed data points.

In one dimensional and two dimensional (1D and 2D) scatter plots, point density creates overlapping marks that makes differentiating individual points difficult. Hover functionality or behaviors in graphical interfaces often attempt to provide detail-on-demand (DOD), but when point density is too great, accurate hover or selection of a desired point becomes impossible to disambiguate.

The system can visualize rectangular data in 1D and 2D scatter and bubble charts as points with radius R (thereby forming a circle with radius R), where the points can correspond to a column in the dataset or can default to a preset value. The system provides a control, such as the user interface element 720, that allows the user to toggle force spread on/off.

When the force spread is toggled on, the system can initialize a force simulation where points are treated as bodies with radius R matching the size of their encoded value in the visualization 700, 730. Thus, each point displayed as a circle with radius R is repelled by its neighboring point by a distance R, so two points (and thus two displayed circles) can be repelled by a total 2R. The force simulation can use a Verlet velocity integrator and body collision. Verlet integration is a numerical method used to integrate Newton's equations of motion. In the simulation, particles attract towards their original location, creating a balance between collision and encoded accuracy. The graphed points can be animated to appear as repelling one another to reflect the position of the underlying simulation as the points move apart and thereby avoid any overlapping points as displayed to a user.

When the force spread is toggled off, the system removes collision forces from the force simulation, and graphed points attract towards their original encoded position. The graphed points animate to reflect the position of the underlying simulation to appear as being attracted to one another.

If the force spread is toggled on again, after the simulation has already been initialized, the system can read collision forces, instead of re-computing them.

The system can optimize various force spread parameters such as force strengths, friction, and system cooldown speed from default values to provide a smooth and pleasing user experience that balances speed of movement with a smoothly animating start and stop effect.

Figure 8A:
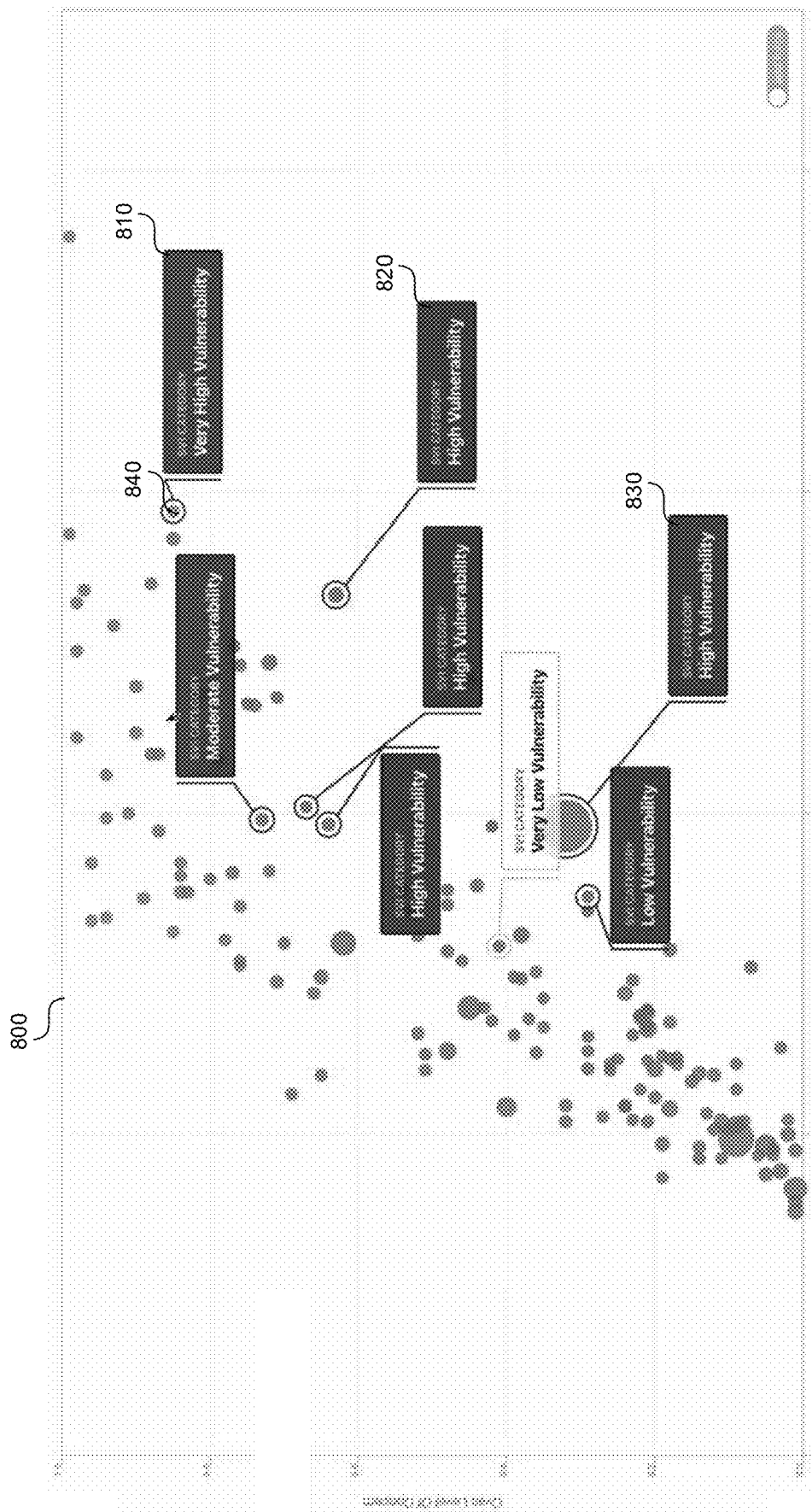
FIG. 8A shows labels associated with a visualization.

FIG. 8A shows labels associated with a visualization. The visualization 800 can include multiple labels 810, 820, 830 (only three labeled for brevity). The system can automatically generate labels in various ways. For example, the user can drag and drop the label from another visualization, or the user can drag-and-drop a label from a suggested list of labels into the visualization 800. The user can click on a particular data element 840, and the system can automatically generate and display a label 810. The labels can be animated, and when the user selects the label, such as by clicking on the label, the system can fix the label to the user-selected position. The system can automatically position the label 810 to avoid collisions between labels and 810, 820, however, the system can also enable the user to change the position of the label. By only displaying certain labels, the system can highlight particular data in the visualization 800.

Figure 8B:
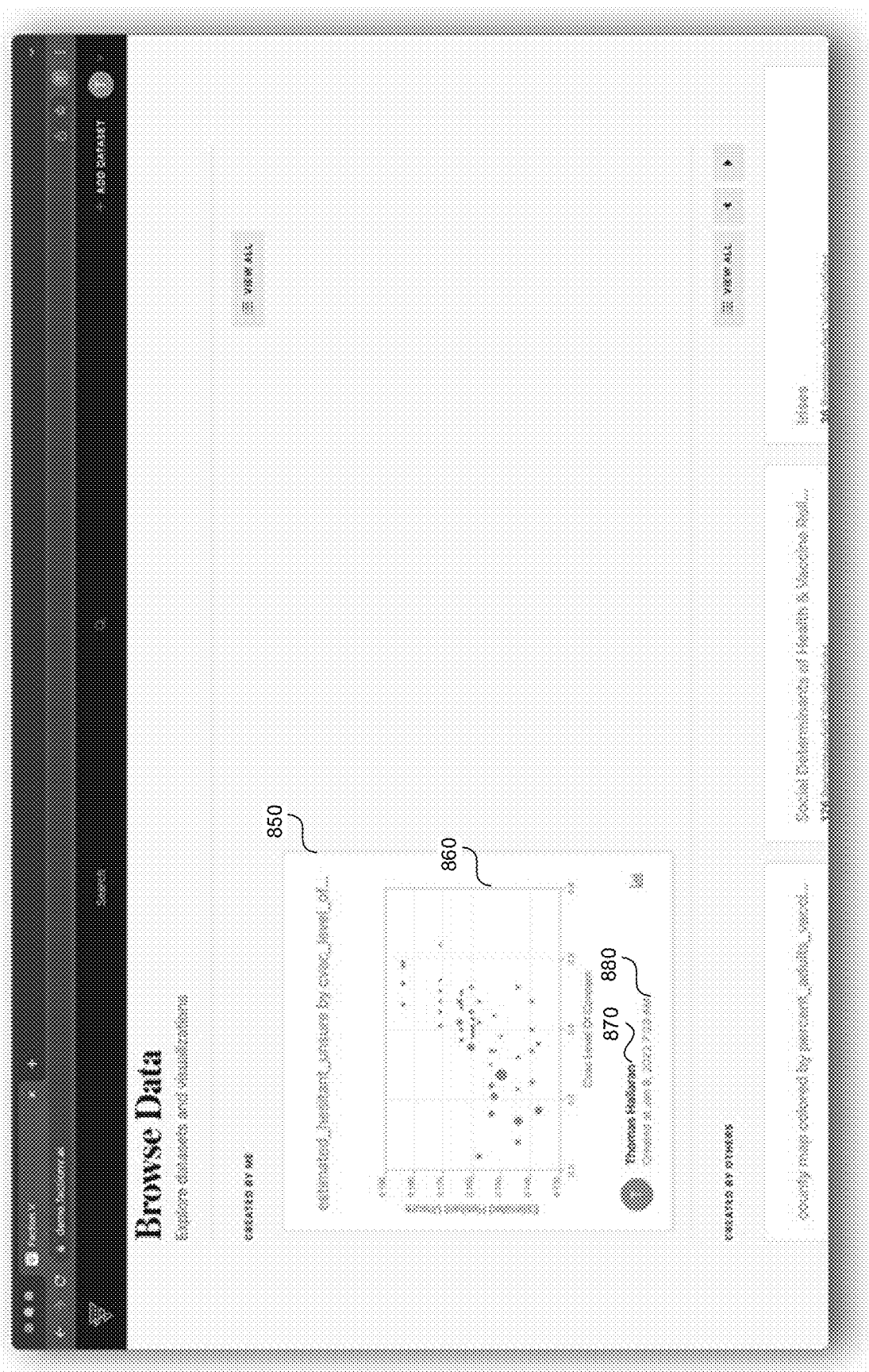
FIG. 8B shows an indication of a folder where a visualization is saved.

FIG. 8B shows an indication of a folder where a visualization is saved. A user can click and save data, such as certain filters and displayed labels. An icon 850 is then displayed to show that a particular visualization has been saved. The icon 850 can indicate the visualization 860, the user 870 creating the visualization, and a date and time 880 when the visualization was created.

Figure 9:
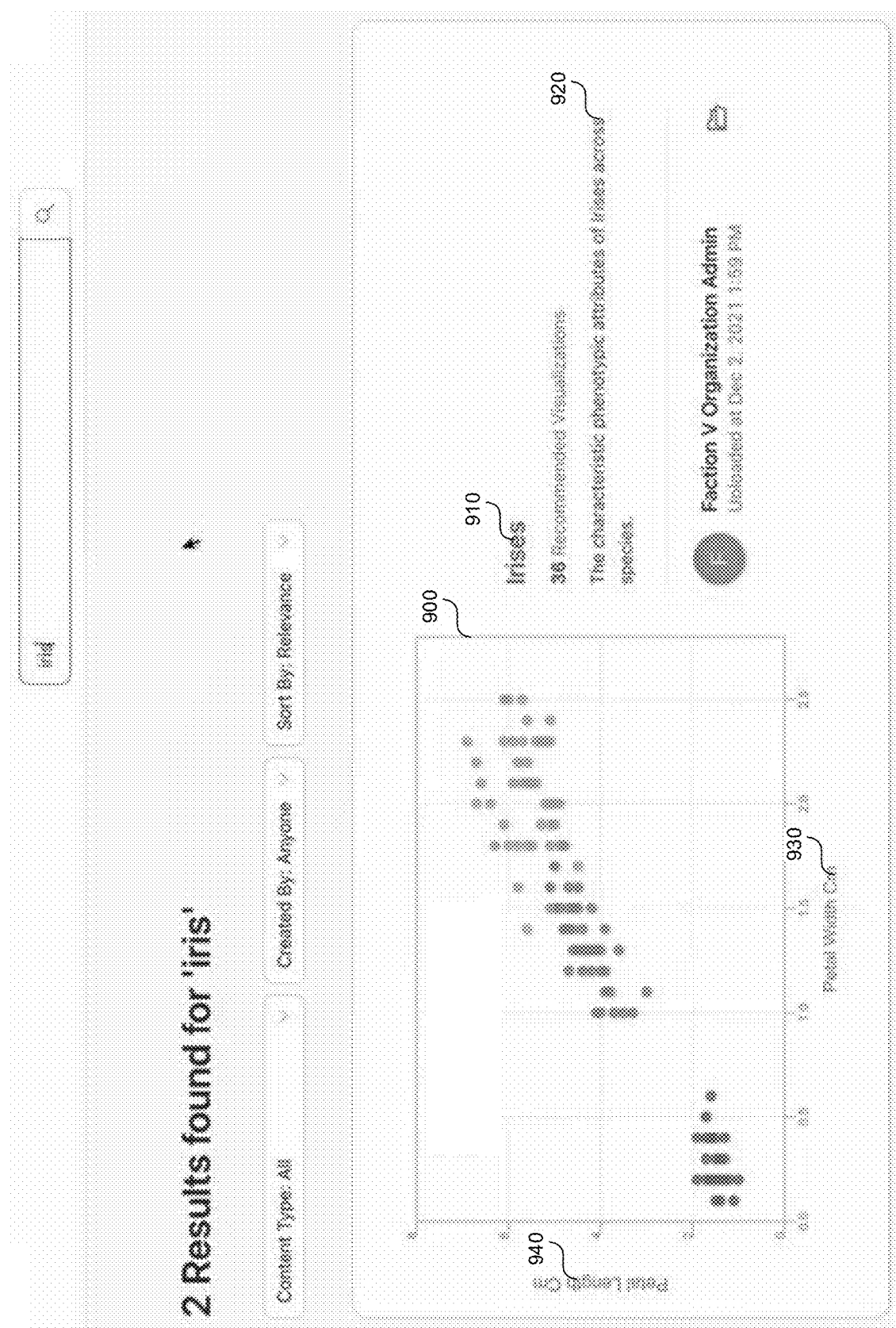
FIG. 9 shows a search functionality.

FIG. 9 shows a search functionality. The search functionality can receive an input from the user and search the visualizations produced by the system to produce the most relevant visualization 900. The system provides various search attributes. The system supports a search by the title 910 or text 920 describing a visualization, by creator of the visualization, by variables 930, 940 presented in the visualization, etc. The system can also present the multiple results sorted by various criteria such as relevance, alphabetically, etc.

Figure 10:
FIG. 10 shows filters that can be applied to a visualization 1000.

FIG. 10 shows filters that can be applied to a visualization 1000. A sidebar 1010 contains filters for the visualized data, which apply to the visualization 1000. The filters can include variables contained in the visualization such as county 1020, date 1030, or death rate 1040 for the example of FIG. 10. The filters can also include types of data contained in the visualization 1000 such as numerical 1050, ordinal 1060, nominal 1070 or geographical 1080.

Numerical data refers to the data that is in the form of numbers, and not in any language or descriptive form. Often referred to as quantitative data, numerical data is collected in number form and stands different from any form of number data types due to its ability to be statistically and arithmetically calculated.

Ordinal data is a categorical, statistical data type where the variables have natural, ordered categories and the distances between the categories are not known. Nominal data is "labeled" or "named" data which can be divided into various groups that do not overlap. Geographical data refers to data and information that has explicit or implicit association with a location relative to Earth.

The user can save the visualization with or without applied filters. When the user saves the visualization, the applied filters and the labels associated with the visualization are also saved. The system can represent the saved visualization by a visualization icon. By clicking the icon, the user can quickly retrieve the saved visualization. The user can also share the visualization, with or without applied filters and labels, with other users.

Figure 11:
FIG. 11 shows a user editing a visualization 1100.

FIG. 11 shows a user editing a visualization 1100. A user can choose labels to show on top of the visualization 1100 in a sidebar 1110, which appear on top of the visualization 1100. The labels can themselves be organized into categories by title 1120, or by value 1130.

Figure 12A:
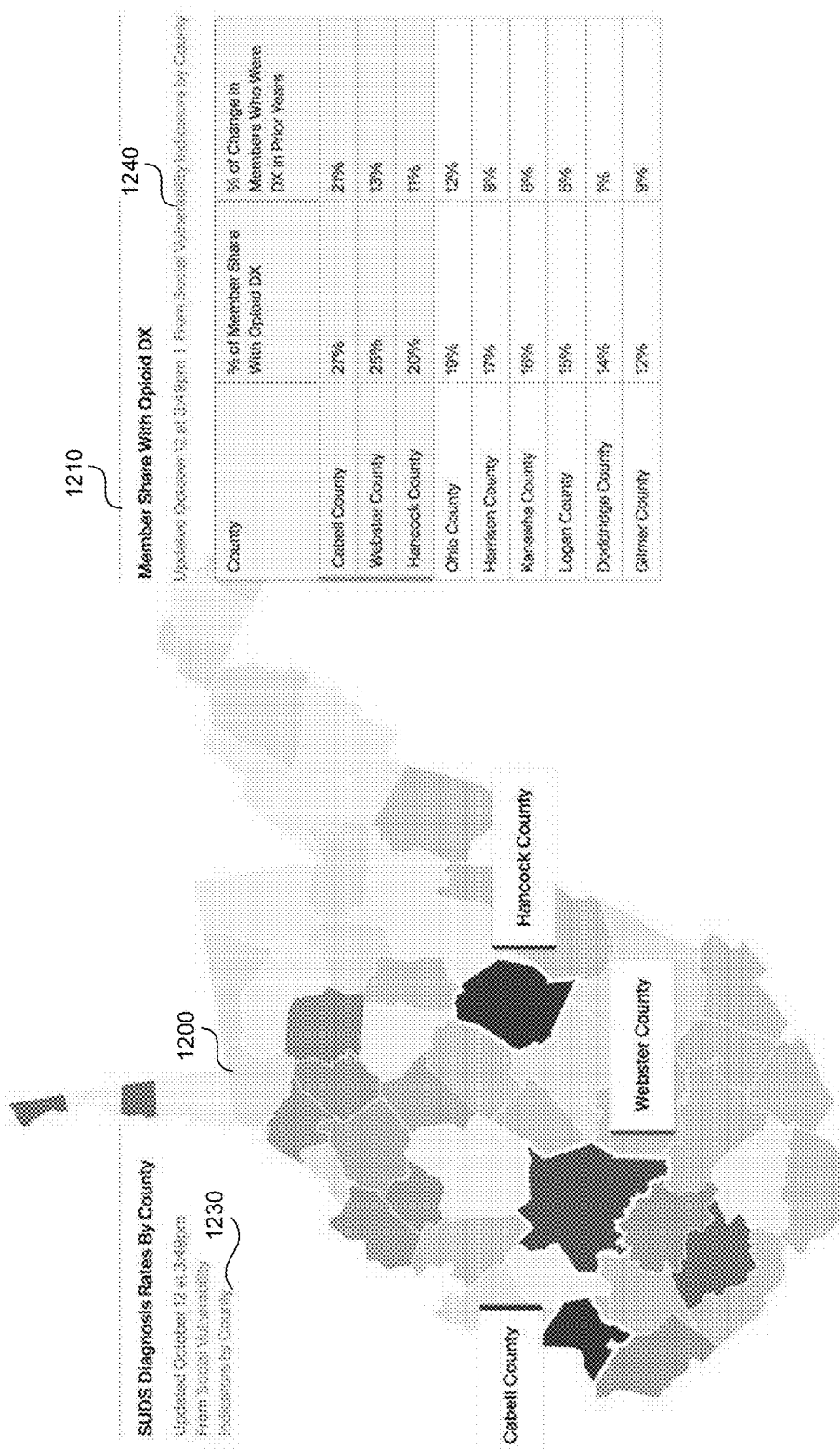
FIGS. 12A-12B show an automatically generated presentation.
Figure 12B:
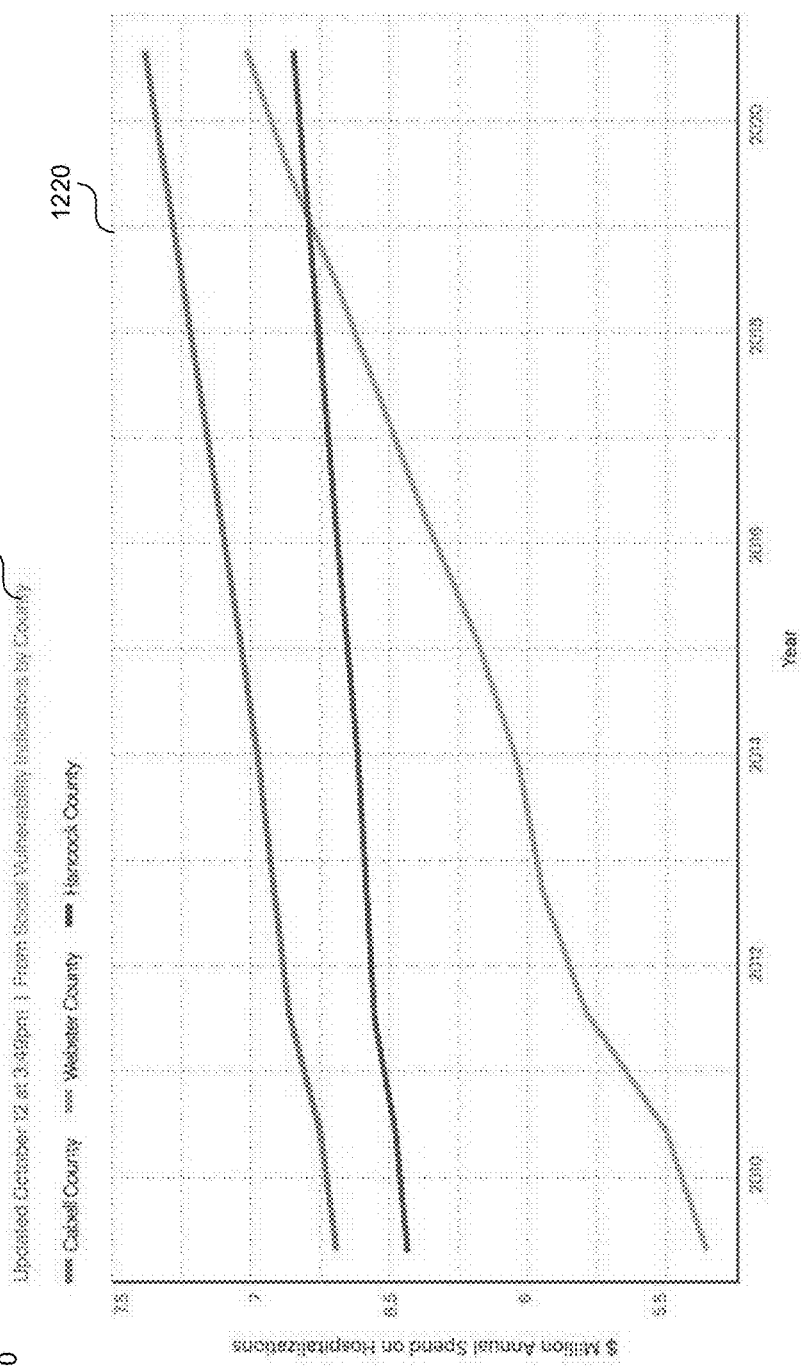

FIGS. 12A-12B show an automatically generated presentation, e.g., a data story. The system can automatically generate a presentation, such as a PowerPoint presentation using visualizations, text, and/or dashboards to describe one or more imported data sets 100 in FIG. 1. The system can generate a hierarchy of data, based on the prioritization of various visualizations, and can create an automatic layout of that data. For example, data with higher priority can appear higher in the hierarchy of data.

For example, visualizations 1200, 1210, 1220 can be individual visualizations produced by the system. The system can automatically lay them out in separate slides, and can combine the visualizations 1200, 1210 into a single slide. The system can also enable the user to generate a new visualization and include the new visualization in the presentation.

The system can automatically provide links 1230, 1240, 1250, 1260 to the data set. When a user clicks on any one of the links 1230, 1240, 1250, 1260 the system can provide the information contained in the data set. The data set can be live and changing. The link 1230, 1240, 1250, 1260 can connect the user to the live data set, or the user can fix the link to the data set recorded at a particular time. The system can display the time when the data set was obtained to thereby indicate to a user/reader how fresh data provided in a visualization is.

The system can change the layout to be vertical or horizontal. For example, visualizations 1200, 1210, 1220 are horizontal, while the text 1270 is vertical. The system can use an AI/ML model to generate the appropriate text based on the visualization and the associated data set. The appropriate text can include the title 1280 and text 1270 describing the data. The system can automatically highlight and adjust the font size of various portions of the text 1270.

The system can receive a query from the user asking why a particular visualization has a particular priority. The system can provide an explanation to the user including the factors used in determining the ranking.

Figure 13:
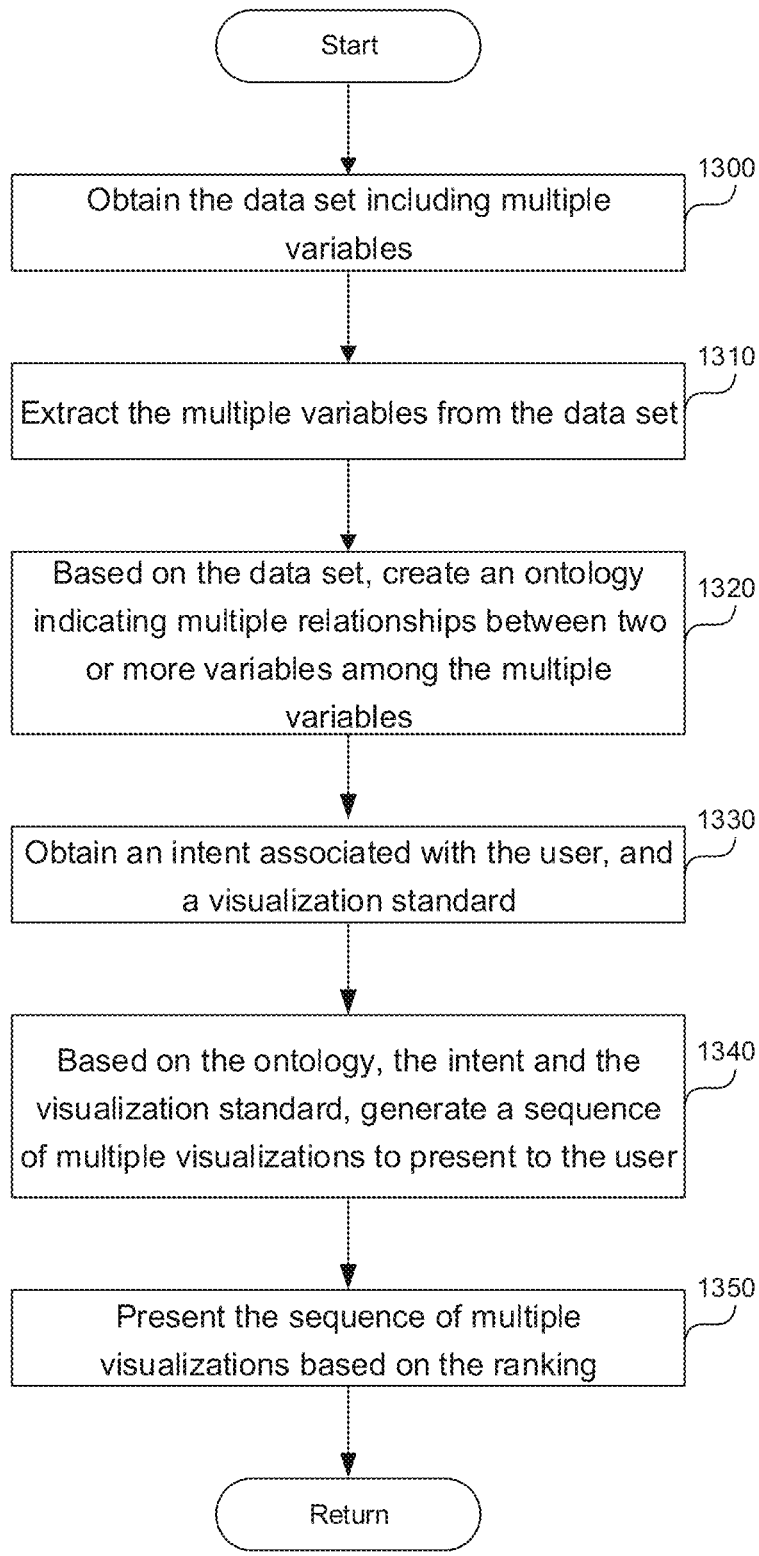
FIG. 13 is a flowchart of a method to generate a visualization of at least a portion of a data set, such as a healthcare data set.

FIG. 13 is a flowchart of a method to generate a visualization of at least a portion of a data set, such as a healthcare data set. In step 1300, a hardware or software processor performing the instructions described in this application can obtain the data set including multiple variables. In step 1310, the processor can extract the multiple variables from the data set.

In step 1320, based on the data set, the processor can create an ontology indicating multiple relationships between two or more variables among the multiple variables, where a relationship among multiple relationships indicates a correlation between the two or more variables. The ontology can indicate a dependent and an independent variable among multiple variables. For example, the dependent/independent relationship can be represented by a direction of an edge 530 in FIG. 5. An independent variable can be a source of the edge 530, while the dependent variable can be the destination of the edge. Further, the ontology can indicate a subset of variables among the multiple variables to aggregate.

In step 1330, the processor can obtain an intent associated with the user and a visualization standard. The intent associated with the user can include a user role within an organization. The visualization standard can indicate a visual attribute associated with the visualization such representing categorical variables using a bar graph and/or representing numerical variables using a scatterplot.

In step 1340, based on the ontology, the intent and the visualization standard, the processor can generate a sequence of multiple visualizations to present to the user. The processor can determine the multiple visualizations to present to the user by determining multiple permutations of the two or more variables. In each permutation, a different variable is assigned to the X-axis or to a Y-axis. A permutation among the multiple permutations of the two or more variables corresponds to a visualization among the multiple visualizations. For example, if the data set contains 20 variables, the number of possible permutations of two-dimensional visualizations that can be generated is 20*19=380. If the processor is generating a multidimensional visualization, the number of visualizations increases drastically. For example, if the processor is considering just permutations of two variables and three variables, the number of visualizations that can be generated becomes 20*19+20*19*18=7220. If the system evaluates the space of higher dimensional visualizations as well, and includes 4 and 5 number combinations, the visualization space grows to 1,983,980.

The processor can rank the multiple visualizations based on the correlation between the two or more variables, the visualization standard and the intent associated with the user. Based on the ranking, the processor can present only the top ranked permutations. Finally, in step 1350, the processor can present the sequence of multiple visualizations based in the order of ranking.

The processor can generate a visualization of any set of variables, such as healthcare variables shown herein. The processor can obtain the healthcare data set indicating a maternity cost, gender, age, geographical location, and health risk associated with maternity. Based on the ontology, the processor can create an aggregate variable including age, geographical location, and health risk associated with maternity. The processor can generate a visualization of the maternity cost and the aggregate variable.

The processor can determine the user intent in various ways. For example, the processor can determine a role associated with the user within an organization, where the role indicates a proficiency associated with the user in interpreting a visualization, and where the proficiency includes high proficiency or a low proficiency. Upon determining that the proficiency is high, the processor can generate a visualization among multiple visualizations including more variables than when the proficiency is low.

In another example, to determine the user intent, the processor can determine a task performed on the data set. The processor can determine whether the task performed of the data set includes an opportunity analysis. Upon determining that the task form of the data set includes the opportunity analysis, the processor can increase ranking of a visualization showing dispersion and/or variation.

In a third example, to determine the user intent, the processor can determine a chart frequently used by the user. The processor can assign a higher ranking to the chart frequently used by the user.

To rank multiple visualizations, the processor can obtain a degree of correlation between the two or more variables. The processor can determine an existence of an outlier value between the two or more variables. The processor can determine a type associated with the two or more variables, where the type includes numerical data or categorical data. Based on the degree of correlation, the existence of the outlier value, the type associated with two or more variables, and the user intent, the processor can rank the multiple visualizations. The processor can present visualizations with higher ranking.

The processor can obtain the visualization standard indicating to include time on an X-axis, to present a categorical variable using a bar graph, and to present a numerical variable using a scatterplot. The visualization standard can also include a color range. The processor can generate a visualization in the sequence of multiple visualizations conforming to the visualization standard.

The processor can use other attributes of the visualization such as size, color, and/or opacity to present additional variables in the visualization. The processor can obtain the visualization standard indicating an attribute to vary based on the two or more variables, where the attribute includes size, color, and opacity. The processor can obtain a predetermined range associated with the attribute. The processor can determine a range associated with a variable among the two or more variables. The processor can map the predetermined range associated with the attribute to the range associated with the variable. Based on the mapping, the processor can present the attribute in a visualization in the sequence of multiple visualizations conforming to the visualization standard.

The processor can enable the user to merge two data sets. The processor can obtain a second data set. The processor can generate a second sequence of multiple visualizations to present to the user based on the second data set. The processor can receive from the user an indication of a second visualization in the second sequence of multiple visualizations and a first visualization in the first sequence of multiple visualizations. The processor can create a third visualization based on the second visualization and the first visualization. If the two visualizations are not compatible, such as when two visualizations do not share any common variables, the processor can produce an error and not generate the third visualization.

In addition, when merging two data sets, the system can analyze the visualizations in each data set, and recommend which visualizations from which data set can be joined. For example, the system can identify common variables in the visualizations, and recommend joining visualizations having at least one common variable.

The processor can create a presentation, such as a data story. The processor can create a presentation based on the multiple visualizations by allowing the user to select a visualization among the multiple visualizations. Upon selection, the processor can automatically adjust the layout of the presentation to include the visualization. The processor can create a link associated with the visualization, where upon selection of the link a portion of the healthcare data set associated with the visualization is presented to the user. In addition, the processor can enable the user to edit/create their own tables.

The processor can provide a search functionality to search the multiple visualizations using a search query. The processor can find multiple matching visualizations corresponding to the search query. The processor can present a visualization having highest-ranking among the multiple matching visualizations.

Computer System

Figure 14:
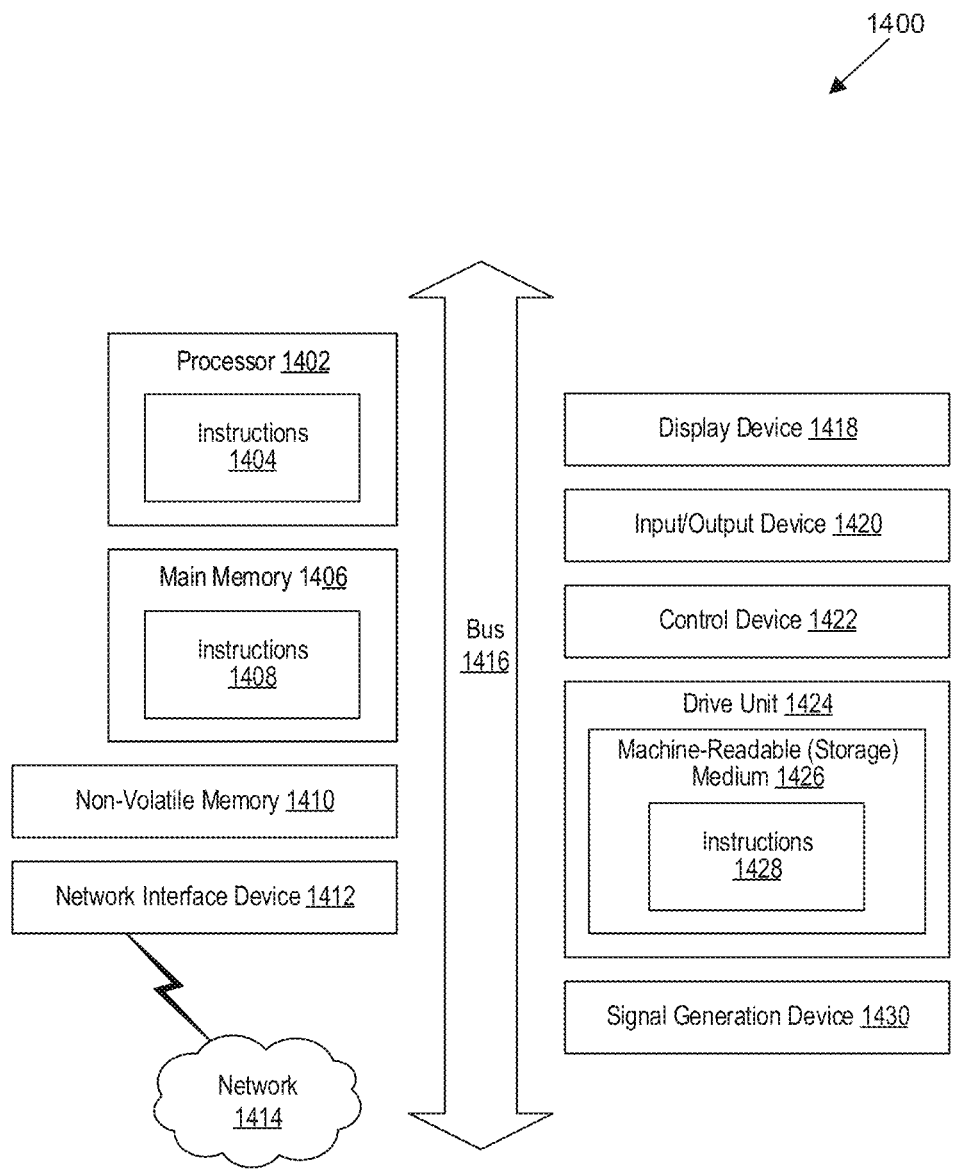
FIG. 14 is a block diagram that illustrates components of a computing device.

FIG. 14 is a block diagram that illustrates an example of a computer system 1400 in which at least some operations described herein can be implemented. As shown, the computer system 1400 can include: one or more processors 1402, main memory 1406, non-volatile memory 1410, a network interface device 1412, video display device 1418, an input/output device 1420, a control device 1422 (e.g., keyboard and pointing device), a drive unit 1424 that includes a storage medium 1426, and a signal generation device 1430 that are communicatively connected to a bus 1416. The bus 1416 represents one or more physical buses and/or point-to-point connections that are connected by appropriate bridges, adapters, or controllers. Various common components (e.g., cache memory) are omitted from FIG. 14 for brevity. Instead, the computer system 1400 is intended to illustrate a hardware device on which components illustrated or described relative to the examples of the Figures and any other components described in this specification can be implemented.

The computer system 1400 can take any suitable physical form. For example, the computing system 1400 can share a similar architecture as that of a server computer, personal computer (PC), tablet computer, mobile telephone, game console, music player, wearable electronic device, network-connected ("smart") device (e.g., a television or home assistant device), AR/VR systems (e.g., head-mounted display), or any electronic device capable of executing a set of instructions that specify action(s) to be taken by the computing system 1400. In some implementation, the computer system 1400 can be an embedded computer system, a system-on-chip (SOC), a single-board computer system (SBC) or a distributed system such as a mesh of computer systems or include one or more cloud components in one or more networks. Where appropriate, one or more computer systems 1400 can perform operations in real-time, near real-time, or in batch mode.

The network interface device 1412 enables the computing system 1400 to mediate data in a network 1414 with an entity that is external to the computing system 1400 through any communication protocol supported by the computing system 1400 and the external entity. Examples of the network interface device 1412 include a network adaptor card, a wireless network interface card, a router, an access point, a wireless router, a switch, a multilayer switch, a protocol converter, a gateway, a bridge, bridge router, a hub, a digital media receiver, and/or a repeater, as well as all wireless elements noted herein.

The memory (e.g., main memory 1406, non-volatile memory 1410, machine-readable medium 1426) can be local, remote, or distributed. Although shown as a single medium, the machine-readable medium 1426 can include multiple media (e.g., a centralized/distributed database and/or associated caches and servers) that store one or more sets of instructions 1428. The machine-readable (storage) medium 1426 can include any medium that is capable of storing, encoding, or carrying a set of instructions for execution by the computing system 1400. The machine-readable medium 1426 can be non-transitory or comprise a non-transitory device. In this context, a non-transitory storage medium can include a device that is tangible, meaning that the device has a concrete physical form, although the device can change its physical state. Thus, for example, non-transitory refers to a device remaining tangible despite this change in state.

Although implementations have been described in the context of fully functioning computing devices, the various examples are capable of being distributed as a program product in a variety of forms. Examples of machine-readable storage media, machine-readable media, or computer-readable media include recordable-type media such as volatile and non-volatile memory devices 1410, removable flash memory, hard disk drives, optical disks, and transmission-type media such as digital and analog communication links.

In general, the routines executed to implement examples herein can be implemented as part of an operating system or a specific application, component, program, object, module, or sequence of instructions (collectively referred to as "computer programs"). The computer programs typically comprise one or more instructions (e.g., instructions 1404, 1408, 1428) set at various times in various memory and storage devices in computing device(s). When read and executed by the processor 1402, the instruction(s) cause the computing system 1400 to perform operations to execute elements involving the various aspects of the disclosure.

Remarks

The terms "example", "embodiment" and "implementation" are used interchangeably. For example, reference to "one example" or "an example" in the disclosure can be, but not necessarily are, references to the same implementation; and such references mean at least one of the implementations. The appearances of the phrase "in one example" are not necessarily all referring to the same example, nor are separate or alternative examples mutually exclusive of other examples. A feature, structure, or characteristic described in connection with an example can be included in another example of the disclosure. Moreover, various features are described which can be exhibited by some examples and not by others. Similarly, various requirements are described which can be requirements for some examples but no other examples.

The terminology used herein should be interpreted in its broadest reasonable manner, even though it is being used in conjunction with certain specific examples of the invention. The terms used in the disclosure generally have their ordinary meanings in the relevant technical art, within the context of the disclosure, and in the specific context where each term is used. A recital of alternative language or synonyms does not exclude the use of other synonyms. Special significance should not be placed upon whether or not a term is elaborated or discussed herein. The use of highlighting has no influence on the scope and meaning of a term. Further, it will be appreciated that the same thing can be said in more than one way.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import can refer to this application as a whole and not to any particular portions of this application. Where context permits, words in the above Detailed Description using the singular or plural number may also include the plural or singular number respectively. The word "or" in reference to a list of two or more items covers all of the following interpretations of the word: any of the items in the list, all of the items in the list, and any combination of the items in the list. The term "module" refers broadly to software components, firmware components, and/or hardware components.

While specific examples of technology are described above for illustrative purposes, various equivalent modifications are possible within the scope of the invention, as those skilled in the relevant art will recognize. For example, while processes or blocks are presented in a given order, alternative implementations can perform routines having steps, or employ systems having blocks, in a different order, and some processes or blocks may be deleted, moved, added, subdivided, combined, and/or modified to provide alternative or sub-combinations. Each of these processes or blocks can be implemented in a variety of different ways. Also, while processes or blocks are at times shown as being performed in series, these processes or blocks can instead be performed or implemented in parallel, or can be performed at different times. Further, any specific numbers noted herein are only examples such that alternative implementations can employ differing values or ranges.

Details of the disclosed implementations can vary considerably in specific implementations while still being encompassed by the disclosed teachings. As noted above, particular terminology used when describing features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed herein, unless the above Detailed Description explicitly defines such terms. Accordingly, the actual scope of the invention encompasses not only the disclosed examples, but also all equivalent ways of practicing or implementing the invention under the claims. Some alternative implementations can include additional elements to those implementations described above or include fewer elements.

Any patents and applications and other references noted above, and any that may be listed in accompanying filing papers, are incorporated herein by reference in their entireties, except for any subject matter disclaimers or disavowals, and except to the extent that the incorporated material is inconsistent with the express disclosure herein, in which case the language in this disclosure controls. Aspects of the invention can be modified to employ the systems, functions, and concepts of the various references described above to provide yet further implementations of the invention.

To reduce the number of claims, certain implementations are presented below in certain claim forms, but the applicant contemplates various aspects of an invention in other forms. For example, aspects of a claim can be recited in a means-plus-function form or in other forms, such as being embodied in a computer-readable medium. A claim intended to be interpreted as a mean-plus-function claim will use the words "means for." However, the use of the term "for" in any other context is not intended to invoke a similar interpretation. The applicant reserves the right to pursue such additional claim forms in either this application or in a continuing application.

We claim:

1. A method to generate a visualization of at least a portion of a data set comprising:
    obtaining, by an algorithm running on a processor, the data set, wherein the data set includes multiple variables;
    extracting, by the algorithm running on the processor, the multiple variables from the data set;
    based on the data set, creating, by the algorithm running on the processor, an ontology indicating multiple relationships between two or more variables among the multiple variables,
        wherein a relationship among multiple relationships indicates a correlation between the two or more variables;
    obtaining, by the algorithm running on the processor, an intent associated with a user,
        wherein the intent associated with the user includes visualizations frequently viewed by the user;
    obtaining, by the algorithm running on the processor, a visualization standard,
        wherein the visualization standard indicates representing categorical variables using a bar graph, and
        wherein the visualization standard indicates representing numerical variables using a scatterplot;
    based on the ontology, the intent and the visualization standard, reducing processing cycles and memory used by the processor by generating, by the algorithm running on the processor, a limited number of relevant visualizations from a large volume of visualizations that can be generated from the data set,
        wherein the limited number of relevant visualizations is presented in a sequence of multiple visualizations to the user by:
            determining, by the algorithm running on the processor, the multiple visualizations to present to the user by determining multiple permutations of the two or more variables,
                wherein a permutation among the multiple permutations of the two or more variables corresponds to a visualization among the multiple visualizations;
            ranking, by the algorithm running on the processor, the multiple visualizations based on the correlation between the two or more variables, the visualization standard and the intent associated with the user; and
    presenting, by the algorithm running on the processor, the sequence of multiple visualizations based on the ranking,
        wherein the sequence of multiple visualizations includes less than all possible visualizations from combinations of the multiple variables.

2. The method of claim 1, comprising:
    obtaining the data set indicating a maternity cost, gender, age, geographical location, and health risk associated with maternity;
    based on the ontology, creating an aggregate variable including age, geographical location, and health risk associated with maternity; and
    generating a visualization of the maternity cost and the aggregate variable.

3. The method of claim 1, comprising:
    obtaining the visualization standard indicating an attribute to vary based on the two or more variables,
        wherein the attribute includes size, color, and opacity;
    obtaining a predetermined range associated with the attribute;
    determining a range associated with a variable among the two or more variables;
    mapping the predetermined range associated with the attribute to the range associated with the variable; and
    based on the mapping, presenting the attribute in a visualization in the sequence of multiple visualizations conforming to the visualization standard.

4. The method of claim 1, comprising:
    creating a presentation based on the multiple visualizations by allowing the user to select a visualization among the multiple visualizations;
    upon selection, automatically adjusting a layout of the presentation to include the visualization; and
    creating a link associated with the visualization,
        wherein upon selection of the link a portion of the data set associated with the visualization is presented to the user.

5. The method of claim 1, comprising:
    obtaining a second data set;
    generating a second sequence of multiple visualizations to present to the user based on the second data set; and
    receiving from the user an indication of a second visualization in the second sequence of multiple visualizations and a first visualization in the sequence of multiple visualizations; and
    creating third visualization based on the second visualization and the first visualization.

6. The method of claim 1, comprising:
    determining a role associated with the user within an organization,
        wherein the role indicates a proficiency associated with the user in interpreting data visualizations,
        wherein the proficiency includes high proficiency or a low proficiency; and
    upon determining that the proficiency is high, generating a visualization among multiple visualizations including more variables than when the proficiency is low.

7. The method of claim 1, comprising:
    determining a task performed on the data set;
    determining whether the task performed on the data set includes an opportunity analysis; and upon determining that the task performed on the data set includes the opportunity analysis, increasing ranking of a visualization showing dispersion.

8. The method of claim 1, wherein ranking the multiple visualizations comprises:
obtaining a degree of correlation between the two or more variables;
determining an existence of an outlier value between the two or more variables;
determining a type associated with the two or more variables, wherein the type comprises numerical data or categorical data; and
based on the degree of correlation, the existence of the outlier value, the type associated with two or more variables, and the user intent, ranking the multiple visualizations.

9. The method of claim 1, comprising:
obtaining the visualization standard indicating to include time on an X-axis, indicating to present a categorical variable using a bar graph, and indicate to present a numerical variable using a scatterplot; and
generating a visualization in the sequence of multiple visualizations conforming to the visualization standard.

10. The method of claim 1, comprising:
providing a search functionality to search the multiple visualizations using a search query;
finding multiple matching visualizations corresponding to the search query; and
presenting a visualization having highest-ranking among the multiple matching visualizations.

11. At least one computer-readable storage medium, excluding transitory signals and carrying instructions, which, when executed by at least one data processor of a system, cause the system to:
obtain, by an algorithm running on a processor, a data set including multiple variables;
extract, by the algorithm running on the processor, the multiple variables from the data set;
based on the data set, create, by the algorithm running on the processor, an ontology indicating multiple relationships between two or more variables among the multiple variables,
wherein a relationship among multiple relationships indicates a correlation between the two or more variables;
obtain, by the algorithm running on the processor, an intent associated with a user, and a visualization standard,
wherein the visualization standard indicates a visual attribute associated with a visualization;
based on the ontology, the intent and the visualization standard, reduce processing cycles and memory used by the processor by generating, by the algorithm running on the processor, a limited number of relevant visualizations from a large volume of visualizations that can be generated from the data set,
wherein the limited number of relevant visualizations is presented in a sequence of multiple visualizations to the user by:
determining, by the algorithm running on the processor, the multiple visualizations to present to the user by determining multiple permutations of the two or more variables,
wherein a permutation among the multiple permutations of the two or more variables corresponds to a visualization among the multiple visualizations;
ranking, by the algorithm running on the processor, the multiple visualizations based on the correlation between the two or more variables, the visualization standard and the intent associated with the user; and
present, by the algorithm running on the processor, the sequence of multiple visualizations based on the ranking.

12. The computer readable medium of claim 11, comprising instructions to create an ontology comprising instructions to:
create an ontology indicating multiple relationships between two or more variables among the multiple variables,
wherein a relationship among multiple relationships indicates a correlation between the two or more variables,
wherein the ontology indicates a dependent and an independent variable among multiple variables, and
wherein the ontology indicates a subset of variables among the multiple variables to aggregate.

13. The computer readable medium of claim 11, comprising instructions to:
determine a role associated with the user within an organization,
wherein the role indicates a proficiency associated with the user in interpreting visualization,
wherein the proficiency includes high proficiency or a low proficiency; and
upon determining that the proficiency is high, generate a visualization among multiple visualizations including more variables than when the proficiency is low.

14. The computer readable medium of claim 11, comprising instructions to:
determine a task performed on the data set;
determine whether the task performed of the data set includes an opportunity analysis; and
upon determining that the task performed on the data set includes the opportunity analysis, increase ranking of a visualization showing dispersion.

15. The computer readable medium of claim 11, comprising instructions to:
determine a chart frequently used by the user; and
assign a higher ranking to the chart frequently used by the user.

16. The computer readable medium of claim 11, instructions to rank the multiple visualizations comprising instructions to:
obtain a degree of correlation between the two or more variables;
determine an existence of an outlier value between the two or more variables;
determine a type associated with the two or more variables,
wherein the type comprises numerical data or categorical data; and
based on the degree of correlation, the existence of the outlier value, the type associated with two or more variables, and the user intent, rank the multiple visualizations.

17. The computer readable medium of claim 11, comprising instructions to:
obtain the visualization standard indicating to include time on an X-axis, indicating to present a categorical variable using a bar graph, and indicate to present a numerical variable using a scatterplot; and generate a visualization in the sequence of multiple visualizations conforming to the visualization standard.

18. The computer readable medium of claim 11, comprising instructions to:
obtain the visualization standard indicating an attribute to vary based on the two or more variables,
wherein the attribute includes size, color, and opacity;
obtain a predetermined range associated with the attribute;
determine a range associated with a variable among the two or more variables;
map the predetermined range associated with the attribute to the range associated with the variable; and
based on the mapping, present the attribute in a visualization in the sequence of multiple visualizations conforming to the visualization standard.

19. A system comprising:
at least one hardware processor; and
at least one non-transitory memory storing instructions, which, when executed by the at least one hardware processor, cause the system to:
obtain a data set including multiple variables;
extract the multiple variables from the data set;
based on the data set, create, by an algorithm running on a processor, an ontology indicating multiple relationships between two or more variables among the multiple variables,
wherein a relationship among multiple relationships indicates a correlation between the two or more variables;
obtain, by the algorithm running on the processor, an intent associated with a user, and a visualization standard,
wherein the visualization standard indicates an attribute associated with the visualization;
reduce processing cycles and memory used by the processor by generating, by the algorithm running on the processor, a limited number of relevant visualizations from a large volume of visualizations that can be generated from the data set,
wherein the limited number of relevant visualizations is presented in a sequence of multiple visualizations to the user by ranking the multiple visualizations based on the correlation between the two or more variables, the visualization standard and the intent associated with the user; and
present, by the algorithm running on the processor, the sequence of multiple visualizations based on the ranking.

20. The system of claim 19, comprising instructions to create an ontology comprising instructions to:
create an ontology indicating multiple relationships between two or more variables among the multiple variables,
wherein a relationship among multiple relationships indicates a correlation between the two or more variables,
wherein the ontology indicates a dependent and an independent variable among multiple variables, and
wherein the ontology indicates a subset of variables among the multiple variables to aggregate.

21. The system of claim 19, comprising instructions to:
determine a role associated with the user within an organization,
wherein the role indicates a proficiency associated with the user in interpreting visualization,
wherein the proficiency includes high proficiency or a low proficiency; and
upon determining that the proficiency is high, generate a visualization among multiple visualizations including more variables than when the proficiency is low.

22. The system of claim 19, comprising instructions to:
determine a task performed on the data set;
determine whether the task performed of the data set includes an opportunity analysis; and
upon determining that the task performed on the data set includes the opportunity analysis, increase ranking of a visualization showing dispersion.

23. The system of claim 19, comprising instructions to:
determine a chart frequently used by the user; and
assign a higher ranking to the chart frequently used by the user.

24. The system of claim 19, instructions to rank the multiple visualizations comprising instructions to:
obtain a degree of correlation between the two or more variables;
determine an existence of an outlier value between the two or more variables;
determine a type associated with the two or more variables, wherein the type comprises numerical data or categorical data; and
based on the degree of correlation, the existence of the outlier value, the type associated with two or more variables, and the user intent, rank the multiple visualizations.

25. The system of claim 19, comprising instructions to:
obtain the visualization standard indicating to include time on an X-axis, indicating to present a categorical variable using a bar graph, and indicate to present a numerical variable using a scatterplot; and
generate a visualization in the sequence of multiple visualizations conforming to the visualization standard.

26. The system of claim 19, comprising instructions to:
obtain the visualization standard indicating an attribute to vary based on the two or more variables,
wherein the attribute includes size, color, and opacity;
obtain a predetermined range associated with the attribute;
determine a range associated with a variable among the two or more variables;
map the predetermined range associated with the attribute to the range associated with the variable; and
based on the mapping, present the attribute in a visualization in the sequence of multiple visualizations conforming to the visualization standard.

* * * * *